United States Patent
McCulloch et al.

(10) Patent No.: US 9,999,545 B2
(45) Date of Patent: Jun. 19, 2018

(54) MODULAR ANTI-FOG GOGGLE SYSTEM

(71) Applicant: Abominable Labs, LLC, Lake Oswego, OR (US)

(72) Inventors: David McCulloch, Lake Oswego, OR (US); Jack Cornelius, Lake Oswego, OR (US)

(73) Assignee: Abominable Labs, LLC, Lake Oswego, OR (US)

( * ) Notice: Subject to any disclaimer, the term of this patent is extended or adjusted under 35 U.S.C. 154(b) by 782 days.

(21) Appl. No.: 14/359,907

(22) PCT Filed: Nov. 22, 2012

(86) PCT No.: PCT/US2012/066434
§ 371 (c)(1),
(2) Date: May 21, 2014

(87) PCT Pub. No.: WO2013/078442
PCT Pub. Date: May 30, 2013

(65) Prior Publication Data
US 2014/0317836 A1    Oct. 30, 2014

Related U.S. Application Data

(60) Provisional application No. 61/563,738, filed on Nov. 25, 2011.

(51) Int. Cl.
*A61F 9/02* (2006.01)
*G02C 11/08* (2006.01)
*H05B 3/86* (2006.01)

(52) U.S. Cl.
CPC ............. *A61F 9/028* (2013.01); *A61F 9/029* (2013.01); *G02C 11/08* (2013.01); *H05B 3/86* (2013.01);
(Continued)

(58) Field of Classification Search
CPC ......... A61F 9/028; A61F 9/029; G02C 11/08; H05B 3/84; H05B 3/86; H05B 2203/005; H05B 2203/014
(Continued)

(56) References Cited

U.S. PATENT DOCUMENTS 1,963,990 A    6/1934   Gilkeson et al.
3,050,736 A    8/1962   Malcolm, Jr.
(Continued)

*Primary Examiner* — Alissa L Hoey
(74) *Attorney, Agent, or Firm* — Howard Russell

(57) ABSTRACT

Modular, anti-fog goggle system comprising: lens with an anti-fog heating element and electrical contact, a semi-rigid anterior body comprising an inner peripheral engagement receptacle for receiving the lens within the body, the lens being releasably retained by a removable lens retaining member preferably comprising a tongue releasably interconnected with a groove in the body, the anti-fog element on the lens being releasably connected with a battery preferably retained within the body, the releasable electrical connection being reinforced by the tongue and groove interconnection, a flexible posterior interface being adapted for interposition between the removable lens retaining member and a user's face, and strap means adapted for holding the goggle on the user's head or helmet and reinforcing the interconnection between the removable lens retaining member and the body.

6 Claims, 22 Drawing Sheets

(52) U.S. Cl.
CPC .. *H05B 2203/005* (2013.01); *H05B 2203/014* (2013.01)

(58) Field of Classification Search
USPC .................................................. 2/435, 443
See application file for complete search history.

(56) References Cited

U.S. PATENT DOCUMENTS

| | | | | |
|---|---|---|---|---|
| 3,160,735 A * | 12/1964 | Aufricht | ............... | G02C 11/08 2/435 |
| 3,896,496 A * | 7/1975 | Leblanc | ................. | A61F 9/025 2/439 |
| 4,150,443 A | 4/1979 | McNeilly | | |
| 4,209,234 A | 6/1980 | McCooeye | | |
| 4,443,893 A | 4/1984 | Yamamoto | | |
| 4,638,728 A | 6/1987 | Elenewski | | |
| 4,682,007 A * | 7/1987 | Hollander | ............. | A42B 3/245 2/435 |
| 4,868,929 A | 9/1989 | Curcio | | |
| 4,942,629 A * | 7/1990 | Stadlmann | ................ | A61F 9/02 2/171.3 |
| 5,093,940 A | 3/1992 | Nishiyama | | |
| 5,363,153 A * | 11/1994 | Bailiff | ................... | G02C 11/00 219/201 |
| 5,410,763 A * | 5/1995 | Bolle | ................. | A61F 9/025 2/436 |
| 5,452,480 A | 9/1995 | Ryden | | |
| 5,459,533 A | 10/1995 | McCooeye et al. | | |
| 5,802,622 A * | 9/1998 | Baharad | ................... | A61F 9/02 2/2.5 |
| 5,815,235 A | 9/1998 | Runckel | | |
| 6,138,286 A * | 10/2000 | Robrahn | ................ | A61F 9/028 2/426 |
| 6,470,696 B1 | 10/2002 | Palfy et al. | | |
| 6,665,885 B2 | 12/2003 | Masumoto | | |
| 6,701,537 B1 * | 3/2004 | Stamp | ..................... | H05B 3/84 2/424 |
| 6,704,944 B2 | 3/2004 | Kawainshi et al. | | |
| 6,772,448 B1 | 8/2004 | Hockaday | | |
| 7,648,234 B2 | 1/2010 | Welchel et al. | | |
| 7,810,174 B2 | 10/2010 | Matera | | |
| 7,856,673 B2 | 12/2010 | Reed | | |
| 8,800,067 B2 * | 8/2014 | Saylor | ..................... | A61F 9/025 2/443 |
| 8,893,314 B2 * | 11/2014 | Chen | ..................... | A61F 9/025 2/426 |
| 9,009,874 B2 * | 4/2015 | McNeal | ................ | A61F 9/028 2/435 |
| 9,532,905 B2 * | 1/2017 | McCulloch | ............ | A61F 9/029 |
| 2002/0157175 A1 | 10/2002 | Dondero | | |
| 2004/0030072 A1 | 3/2004 | Palfy et al. | | |
| 2004/0050072 A1 | 3/2004 | Palfy et al. | | |
| 2007/0279577 A1 | 12/2007 | Stanley et al. | | |
| 2008/0216217 A1 * | 9/2008 | Wang | ..................... | A61F 9/029 2/426 |
| 2008/0290081 A1 | 11/2008 | Biddell | | |
| 2008/0316421 A1 * | 12/2008 | Wang | ..................... | A61F 9/025 351/62 |
| 2009/0151057 A1 | 6/2009 | Lebel et al. | | |
| 2011/0126345 A1 * | 6/2011 | Matsumoto | ............ | A61F 9/028 2/435 |
| 2011/0225709 A1 | 9/2011 | Saylor et al. | | |
| 2013/0091623 A1 * | 4/2013 | McCulloch | ............ | A61F 9/025 2/435 |
| 2015/0121610 A1 * | 5/2015 | Cornelius | ................ | A61F 9/04 2/435 |
| 2015/0238361 A1 * | 8/2015 | McCulloch | ............ | A61F 9/029 2/435 |
| 2016/0070120 A1 * | 3/2016 | Cornelius | ............ | A61F 9/029 219/211 |

* cited by examiner

MODULAR ANTI-FOG GOGGLE SYSTEM

CROSS-REFERENCE TO RELATED APPLICATION

This patent application claims the benefit and priority of U.S. Provisional Patent Application No. 61/563,738 filed Nov. 25, 2011.

FIELD

This invention relates generally to goggles and more particularly to a relatively inexpensive modular anti-fog goggle system with easily interchangeable lenses adapted to particular weather, lighting and fogging conditions.

BACKGROUND

Goggle Construction Generally

Sport goggles, such as are often used for skiing, cycling, snow-boarding, motorcycle and ATV riding, paint-balling, or standard-issue military goggles used primarily for military ground operations, typically have comprised a plastic frame or body and clear plastic, or polycarbonate, see-through lens. Sometimes the plastic body has further been comprised of an anterior body interconnected to a posterior body, the foremost portion of the anterior body being designed for attachment to, carrying and positioning of the lens a comfortable distance from a user's eyes. The posterior body has comprised a foam rubber interface on the most posterior portion thereof for comfortable positioning of the body on the user's face around and defining the field of vision for the user's eyes. Such conventional goggles have further comprised an elongated, elastomeric strap attached at either end thereof to corresponding ends of the anterior body for the purpose of holding the goggles on the head, or helmet, of the user by stretching the strap around the back of the head, or helmet, with the goggle positioned in opposing fashion on the face of the user. It has generally been accepted and understood among goggle wearers that different colors of lenses have been advantageous for different lighting and weather conditions.

The Need for Easily Interchangeable Lenses in Goggles

Earlier conventional goggles have not provided for interchangeable lenses. Not only has this resulted in a much less useful goggle as changing lighting conditions through the day have rendered a current goggle unsuitable for more easily distinguishing variations in terrain, especially snowy terrain of mostly a single color often having only slight shadows on the surface thereof to determine the presence of variations, but where the lens of the goggle has become damaged, or broken, such goggles have required replacement of the entire goggle.

More recently, conventional goggles have allowed for replacement of a damaged or broken lens, or replacement of a lens that is no longer suitable for changed lighting conditions. In such goggles, the body has comprised a flexible, but resilient, molded material forming a relatively deep vertically-oriented groove, often together with a plurality of notches on the lens matched with pegs in the groove for alignment and retention purposes. The notches and matched pegs have been designed to receive and hold the peripheral edge of the lens in a vertically-oriented fashion in the groove and to retain the lens in proper orientation on the pegs relative to the body.

When a user has desired to remove such a lens, they have pulled the flexible body members apart, disconnecting the notches and otherwise disassociating the lens from the groove in the body. Replacement with a different color lens has involved a reverse process of aligning the edge of the lens, and its notches, with their associated groove and pegs, first fitting an upper, or alternatively lower, portion of the lens into its associated groove and pegs, and then fitting the opposite portion of the lens into its associated groove and pegs. This process has been time-consuming and cumbersome, making it difficult for a user to easily interchange lenses, so much so that many have determined to not make an attempt to change the lens in the open, but rather to use a lens that has provided multi-purpose, though not ideal, use for most lighting conditions. Alternatively, where users have shown the patience necessary to have repeatedly changed lenses, these goggle bodies have lost some resiliency, broken, or cracked, due to repeated stressing of the bodies, and this has led to a lack of a sealed engagement between the lens and the body.

Responsive to the difficulties of interchanging lenses for these types of goggles, there have been developed goggles having articulated frames designed for opening and closing to allow easier changing to lenses adapted for changed conditions. An example of such a frame is provided by U.S. Pat. No. 5,815,235, to Runckel, for Ski Goggles With Pivotal Frame Members For Interchanging Lenses. Similarly, published US Patent Application No. US20110225709A1, to Saylor et al., for Eyewear With Interchangeable Lens Mechanism, has facilitated the interchanging of lenses of such goggles with a biased outrigger, gate or latch for securing the lens relative to the goggle, the lens being further held in a proper orientation by one or more engagement members aligned with an aperture, or apertures, in the lens.

The Need for Anti-Fog Means in Goggles

Goggles are known to have become obscured with moisture when temperature and relative humidity conditions inside of the space defined between the goggle body and the user's face and eyes have been such that a dew point has been reached and condensation has formed like a "fog" on the inner surface of the goggle. This typically has happened when a colder inner surface of the goggle lens has come in contact with a now warmer and more humid area enclosed within the goggle body. There are many possible conditions which may lead to fogging of a goggle, since the dew point of the inside of the lens is affected by varying temperature, moisture, pressure and ventilation conditions. One common example of fogging has occurred when a person who has been skiing, cycling, hiking or engaging in other strenuous activity, stops moving as quickly as before, reducing the amount of air flow over the surfaces of the goggle, such that temperature differentials between the inner surface of the goggle and the now warmed and moist air within the goggle caused by the physical exertion and the enclosed space of the goggle have caused fogging.

Another example of fogging involves a significant increase in activity, increasing the amount of moisture and heat trapped within the goggle, primarily from perspiration and also from a higher incidence of exhaling moist warm air that is associated with such physical exertion. In such a case there has existed a greater imbalance in temperature between the inner surface of the goggle lens and the warm, moist air now trapped within the goggle, causing condensation and resulting fogging of the inner surface of the goggle lens.

Thus, fogging is a very common problem with goggles and this has occurred in various situations involving temperature extremes, and particularly warmer temperatures caused by perspiration and respiration entering within the goggle enclosure and which are warmer relative to colder temperature conditions outside of the goggle body. Of course this problem has ranged from being annoying to the user, to presenting a very dangerous situation where the user's field of vision has been greatly diminished while the user has been traveling at high speeds among fixed obstacles, such as trees, widely varying terrain such as bumps, cliffs, or other participants, or the user has otherwise been unable to clearly see an intended target or an enemy combatant. The problem of fogged goggles has resulted in injury and even death among goggle users.

Responsive to this common, annoying and even dangerous condition, great attention has been paid to solutions to the problem of fogging of goggles. For instance, numerous efforts have been made to increase the amount of passive airflow into the goggle. Examples of such may be found in US Patent Application Serial No. 20050193478 to Hussey, for Goggle Attachment System, and U.S. Pat. No. 6,665,885 to Masumoto, for Goggles.

Despite best efforts to produce a goggle that utilizes passive air-flow means for defogging the lens of the goggle, there are often present conditions which have rendered passive air-flow means of de-fogging ineffective. Such conditions have overwhelmed the ability of the passive means to overcome the temperature and humidity differentials presented by exertion by a user in cold, icing conditions or accumulation of snow clogging ventilation means. Also, sometimes a user's clothing, especially such as scarves or face masks, have impeded intended airflow of such goggles, rendering them ineffective. Finally, a problem with passive anti-fogging systems is that, since they have depended upon a larger air space between the user's face and the lens inner surface to create adequate airflow to attempt to overcome dew point, they have not been well-suited for corrective lens applications requiring a smaller and more consistent distance between the user's eyes and the lens. Additionally, the larger air space and distance requirements between the users face and the lens for this type of passive air-flow anti-fog goggle has limited the field of vision of users of such goggles.

As a result, there have even been developed goggles with active, personal fans to ventilate the enclosed space within and the inner surface of the lens of the goggle to mitigate the conditions leading to fogging. An example of such a system has been provided in U.S. Pat. No. 5,452,480, to Ryden, for Ski Goggles. One problem of such a device is that it does not necessarily overcome icing, snow accumulation or other blockage of outer goggle vents, thus rendering such a system less effective. Such goggles still have suffered from the higher volume of airspace between the user's face and the goggle lens, thus leading to inapplicability of such systems to corrective lens wearing situations.

Regardless of the exact causes of fogging of a goggle in a particular situation, it has become understood that sufficient heating of the inner surface of the lens of the goggle comprises an effective means of removing fog from the lens and preventing further fogging. Accordingly, there have been developed various means of actively heating the inner surface of the goggle lens. One such means has comprised the placement of wires, or a resistive gel surface, on the inner surface of the goggle lens, which wires or resistive surface have been attached to an electrical power source such as a DC battery carried on the goggle headband or jacket of the user in order to provide sufficient power to heat the leans. Examples of such a method of heating the lens of the goggle have been disclosed in U.S. Pat. No. 4,868,929, to Curcio, for Electrically Heated Ski Goggles, U.S. Pat. No. 5,459,533, to McCooeye et al., for Defogging Eye Wear, and Published US Patent Application Serial No. US20090151057, to Lebel et al., for Reversible Strap-Mounting Clips for Goggles.

Thus, while there have been devised independent solutions to a need for easily interchanging the lens on a sport or standard-issue military goggle and the need for maintaining such a goggle fog free, there yet exists a need for a sport or standard-issue military goggle that provides not only an easily interchangeable lens system, but also provides an active, effective means of heating the lens to prevent fogging. The lack of interchangeability of lenses and higher manufacturing costs associated with such prior art active heating element-type goggles has greatly limited their suitability for corrective lens wearing applications. Thus, in particular, there exists a need for an efficient and effective means of both releasably attaching the lens of a goggle to its body and therefore preferably allowing for efficient, simultaneous interconnection of the lens to a source for heating of the lens when necessary to prevent fogging. Ideally, such a system would be easy to operate, even with a gloved hand, and would be provided in a goggle that is relatively inexpensive to manufacture, and is thus affordable, for sporting and standard issue military ground operation applications.

Other Goggle Features

Not only have prior art anti-fog goggles lacked the combination of a readily removable and replaceable lens that easily attaches and detaches from a battery power source retained on, or within, the goggle body, but such has not been provided together with such features as on-board on/off switching, onboard battery status indication, and onboard adjustment of the heat to have been applied to the lens to prevent fogging.

Thus, prior art anti-fog goggles have been more cumbersome to use since they have included a detached, remote battery that the user has been required to carry either in a pocket or with a clip on a goggle strap. The battery for such prior art anti-fog goggles has required wiring external of the goggle body for connection to the remote battery.

SUMMARY

In accordance with a first aspect of the invention, there is provided a modular, anti-fog goggle system comprising: a lens having an anti-fog heating element with an electrical contact thereon and further comprising first and second ends, an anterior surface, a posterior surface, and a peripheral edge adapted for being releasably retained in a body of the goggle a distance from a user's eyes so as to provide a shield for the eyes. The goggle further comprises a semi-rigid anterior body further comprising first and second ends and an inner peripheral engagement receptacle adapted for receiving the lens within the body with a portion of the anterior surface of the lens that is adjacent the peripheral edge of the lens engaging the inner peripheral engagement receptacle, the body further comprising a portion of mated retention means attached around an inner periphery of the body. The goggle further comprises a battery adapted for electrical connection to the heating element on the lens and a removable lens retaining member adapted for engaging a portion of the posterior surface of the lens that is adjacent the peripheral edge of the lens and, together with the engagement receptacle of the body, adapted for releasably retaining the lens within the body, the removable lens retaining member further comprising another portion of the mated retention means attached around the periphery of the lens retaining member for releasably interconnecting with the portion of the mated retention means around the inner periphery of the body for retaining the lens within the receptacle within the body when the lens retaining member is installed in the body with the lens retained in the receptacle, the lens being free to be removed from the body upon removal of the lens retaining member. The goggle further comprises an electrical contact on one of the body and the lens retaining member and operatively connected with the battery, wherein upon installation of the removable lens retaining member into the body, the electrical contact on the lens is releasably connected with the electrical contact on one of the body and the lens retaining member adapted for allowing heating of the lens. The goggle further comprises a flexible posterior interface attached to the removable retaining frame member adapted for engaging a user's face adjacent the user's eyes, and a strap means having first and second ends, the first end of the strap means interconnected with the first end of the body, and the second end of the strap means interconnected with the second end of the body, adapted for holding the goggle on one of a user's head and helmet, the strap means further adapted for reinforcing retention of the lens in the body and contact of the electrical contacts on the lens with the battery.

Further, in accordance with this aspect of the invention, there is provided a modular, anti-fog goggle with a removable lens and adapted for accommodating various weather, lighting and fogging conditions. The goggle comprises: a body having a battery and contact therein and further comprising first and second ends, a semi-rigid outer portion defining an outer opening for field of vision and a semi-rigid interior portion defining an inner opening within the outer portion for field of vision and defining a rear-access socket. The goggle further comprises a semi-rigid, semi-transparent lens comprising a peripheral edge, an anterior surface and a posterior surface, the lens residing within the rear-access socket and adapted for being positioned to provide a semi-transparent, shielded view through the outer and inner openings, the lens having a resistive heating element thereon and operatively connected with the battery through the contact. The goggle further comprises retaining means having first and second ends, the retaining means for releasably holding the lens within the rear-access socket and for releasably holding the resistive heating element in electrical contact with the battery. The goggle further comprises a cushioned posterior interface member interposed between one of the lens, the body and the retaining means and a user's face for providing a cushioned structure upon which the goggle is adapted for contacting the user's face, and strap means having first and second ends, the first end of the strap means interconnected with one of the first end of the body and the retaining means, and the second end of the strap means interconnected with one of the second end of the body and the retaining means, the strap means adapted for holding the goggle on a user's head.

This aspect of the invention provides a separate lens and lens retainer member, and it will be appreciated that the face contact member of this aspect of the invention may be glued or otherwise attached to the lens retainer member.

In accordance with this aspect of the invention there is provided an alternate embodiment of a modular, anti-fog goggle system comprising: a battery and a semi-rigid anterior body further comprising first and second ends, a receptacle adapted for receiving a lens and lens retaining member within said body, a portion of mated retention means attached around an inner periphery of said body and an electrical contact electrically connected to said battery. This embodiment of the invention further comprises a removable lens having an anti-fog heating element with an electrical contact thereon and further comprising first and second ends, an anterior surface, a posterior surface, and a peripheral edge. The removable lens in accordance with this embodiment of the invention further comprises a retaining member attached around the peripheral edge of the lens, the lens retaining member further comprising another portion of mated retention means attached around the periphery of the lens retaining member for releasably interconnecting with the portion of the mated retention means around the inner periphery of the body for retaining the lens and lens retaining member within the receptacle within the body with the lens positioned in front of a user's eyes so as to provide a shield for the eyes, wherein upon interconnecting of the lens retaining member with the body, the electrical contact on the lens is releasably connected with the electrical contact on the body allowing heating of the lens. The goggle further comprises a flexible posterior interface attached to the removable lens retaining member adapted for engaging a user's face adjacent the user's eyes and strap means having first and second ends, the first end of the strap means interconnected with the first end of the body, and the second end of the strap means interconnected with the second end of the body, adapted for holding the goggle on one of a user's head and helmet, the strap means further adapted for reinforcing retention of the lens in the body and contact of the electrical contact in the lens with the contact in the body operatively connected with the battery.

Thus, this aspect of the invention provides that the lens and the lens retaining member, as well as the face contact member, are comprised of a single module in that the lens retaining member is attached around the periphery of the lens and the face contact member is preferably glued, or otherwise attached to the posterior of the lens retaining member.

In accordance with either the first or the second aspect and embodiments of the invention, the portion of mated retention means attached around the inner periphery of the goggle body comprises a groove and the portion of mated retention means attached around the periphery of the lens retaining member, whether integrated with the lens, or apart from the lens, comprises a tongue, the groove and tongue portions of the body and the lens retaining member being adapted for releasably interconnecting the body and the lens retaining member to retain the lens within the body and to retain the contact of the heating element on the lens in contact with the electrical contact connected with the battery. Also, preferably, in accordance with either aspect of the invention the goggle is provided with an on/off power switch for turning off power to the heating element of the goggle to conserve battery power as, for example, during storage or other non-use of the goggle.

These first two aspects and embodiments of the invention address and alleviate problems presented by conventional goggles in that they provide for an easily interchangeable lens in a goggle that is also adapted for fog-free wearing pleasure. Thus, users are enabled in easily interchanging one fog-free lens with another fog-free lens to adapt to varying lighting conditions without enduring the hassle associated with conventional goggles to successfully get the lens back in the frame. Further, users are enabled in interchanging a non-fog-free lens with a fog-free lens, as both types of lenses are interchangeable with the present invention. By minimizing the number of steps a user must take to interchange lenses, as well as to use the fog-free characteristics of the present invention, users will be more apt to use and benefit from the features of the improved goggle.

Further, making of the electrical connection with the battery power source with these aspects and embodiments of the invention is essentially simultaneous, or automated, with interchanging of the lens, without any additional steps being further necessary to make the connection for power to the lens. Of course, it may be advantageous to provide an on/off switch on the goggle system to allow conservation of battery power when not in use, but operation of such does not comprise an additional step to interchanging of lenses, since such interchanging may be accomplished with no risk to the user or the system in such a low-voltage power system without first switching off the battery. Further, using the strap in placing the goggles on the user's head serves to reinforce the engagement of the easily interchangeable lens and the body of the goggle and also serves to reinforce the electrical connection between the heating element of the goggle lens and the battery.

A goggle provided in accordance with either of these aspects of the invention is suitable for use with any color or tint of anti-fog lens, it being the case that the user may have at ready whichever type of goggle lens the user needs given weather, lighting and fogging conditions, such as relative humidity inside and outside of the goggle, outside temperature, body temperature, difficulty of terrain leading to greater exertion, and barometric pressure conditions. Of course, if conditions do not require anti-fog capability in the lens, the power to the battery, and thus to the lens, may be easily turned off by toggling the on/off switch. Users of goggles rarely can anticipate with certainty what such conditions will be on any given day, so it is important to have a goggle that is widely adaptable to the many and varied conditions that may be encountered on any given day.

Thus, a goggle in accordance with either of these aspects of the invention is readily adapted for use with fully interchangeable lenses, whether they be lenses for a sunny day with, or without, anti-fog means incorporated, whether they be lenses for a cloudy day with, or without, anti-fog means incorporated, or whether they be lenses adapted for rain, or heavy snow, or some weather condition in-between. In such case the user will be encouraged to make appropriate lens changes, thus contributing to the safety of clearer vision through an appropriately chosen goggle by using the goggle of the invention, because interchanging of the lens and simultaneous interconnection of an electrical heat source to the goggle, when desirable, is assured. Further the invention is readily applicable for vision correcting lenses, since active heating of the lens with the heating element overcomes dew point within the cavity formed between the lens and the user's face preventing fogging of the lens despite smaller volume and areas existing between the lens and the user's face with the present invention. Since the present invention allows for a consistent and smaller distance between the user's face and the lens of the goggle than prior art passive anti-fog lenses, this enables application of the present invention to corrective lens requirements that the corrective lens be close to the user's eyes and consistently spaced therefrom. Still further, because the present invention is modular in allowing easy interchangeability of lenses, the invention is easily adapted for use with separately manufactured corrective, anti-fog lenses that are nevertheless manufactured for use with the goggle. Also, because the lens of the present invention is in close proximity to the user's face, this enables greater field of peripheral vision for the user of the present invention.

In accordance with another aspect of the invention, the battery for heating the lens may be retained on, or preferably within, the body of the goggle. This aspect of the invention adds to the ease of use of the invention, since the user does not need to manage a separate battery pack and there are no external wires interconnecting the goggle and the battery that may become dislodged during the jolting sometimes encountered during strenuous activity, such as skiing or riding of ATVs.

In accordance with another aspect of the invention, there is provided a battery strength indicator means carried on the body of the goggle. This aspect of the invention gives the user the ability to easily determine whether the level of power in the battery is suitable for a desired time for activity, or whether charging of the battery may be necessary before continuing the activity. Such a system of indicating battery strength may comprise an array of LED's or an on-lens display. The LEDs of each array may further comprise temporary visibility of the same within the goggle, as by using square LEDs on the corner of the field of vision of the user, or similarly by using light pipes to direct light to the edge of the field of vision.

In accordance with yet another aspect of the invention, there is provided a heat adjustment means on the body of the goggle which heat adjustment means is operatively connected with the battery. This aspect of the invention provides the ability to increase the level of power to the heating element on the lens of the goggle as necessary to combat fogging of the lens, or even just to warm the face of the user during cold winter days.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings wherein like reference characters refer to like elements.

DESCRIPTION OF EMBODIMENTS

Detached Lens and Retention Member Embodiment

Figure 1:
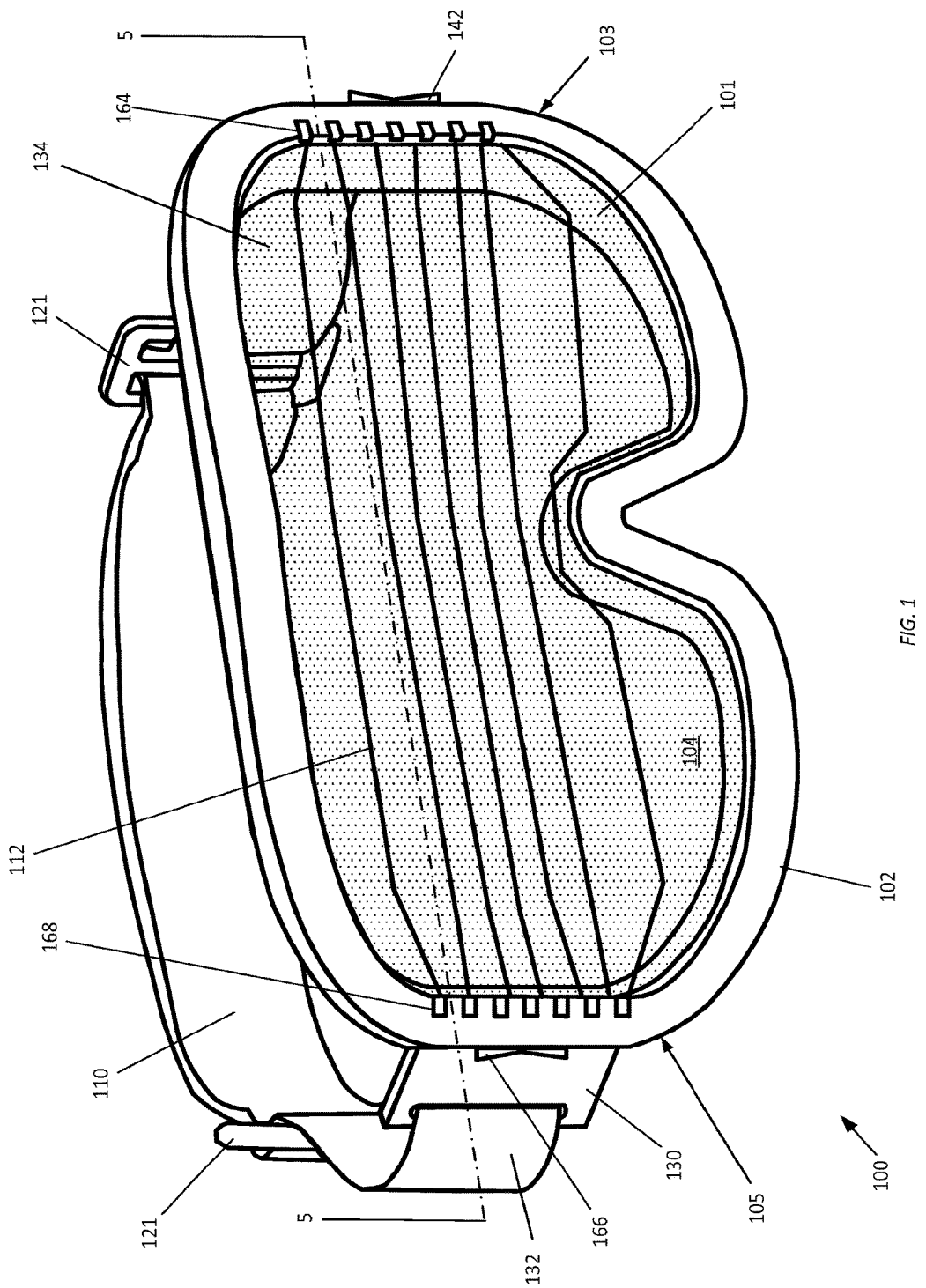
FIG. 1 is a perspective view of a modular, anti-fog goggle in accordance with the first and second embodiments of the invention disclosed.

Referring to FIGS. 1-3c, 4a, 5a-c, and 6a, there is shown a first embodiment of a modular, anti-fog enabled goggle system 100 in accordance with the invention. The goggle 100 in accordance with this first embodiment of the invention further comprises a goggle body 102 having a first, left, body end 103 and a second, right, body end 105, the determination of left and right being made as if looking through the goggle. The goggle 100 further comprises an easily interchangeable lens 104, a flexible, preferably foam rubber, posterior face contact or interface 101 and strap retaining members 130 that depend from the goggle body 102. The goggle 100 further comprises an adjustable strap 110 that has first and second ends 132, 134 attached to the strap retaining members 130 and length adjustment members 121.

Anti-Fog Power and Goggle Feature Control Circuit

Used as an anti-fog goggle, the lens 104 of the goggle 100 further comprises an anti-fog means, such as a heating element 112. To power the heating element 112, as shown primarily in FIGS. 5a-c, 6a, 7 and 8, the anti-fog goggle system 100 further comprises a power and control circuit comprising a double-sided flexible circuit board 148 having thereon one or more power supplies, such as lithium-ion or lithium-polymer batteries 114 with a meltable link, or electronic, fuse 175, commonly available for use with cell phones, the circuit also having thereon an on/off power switch 142 for controlling power to the heating element 112 of the goggle lens 104. Flexible circuit 148 may further comprise a power-level control input device, such as a three-way rocker switch 166, on the flexible circuit for controlling the amount of voltage from the batteries to heat the heating element 112. One or more IC chips 170, 172 are included on the flexible circuit board 148 for control of circuit functions such as on/off control, battery charging control, LED array battery life indicator control, variable voltage/power control and LED array power indicator control. The flexible circuit board 148, the batteries 114 and the other power circuitry described are preferably housed and sealed within body 102 of the goggle 100, the body being sealed with a water-tight seal to prevent intrusion of liquid into the goggle body. The goggle body 102 may comprise an O-ring type seal, or preferably it may be permanently sealed at the time of manufacture to prevent moisture. A power switch 142, such as a rocker switch for turning on and off the anti-fog heating element of the goggle 100, is accessible with the user's finger, the switch being carried on an end, such as left end 103, of the goggle body 102 and operably connected with the flexible circuit board 148.

The basic electronics circuit assembly for the goggle 100 comprises the flexible circuit board 148 having the batteries 114 thereon, the power switch 142, wiring 115, 117 in the goggle body 102, lens contacts 138, 140, corresponding goggle body contacts 139, 141 and the heating element 112 on the lens 104. As will be readily appreciated by those of ordinary skill in the art of such circuit design, some variations in the design of the power circuit may be required, depending upon the specific requirements of the overall system and the type of heating element 112 employed. Thus, as understood by those of ordinary skill in the art, for example, for the resistive-wire version of the goggle 100, the batteries 114 could be employed in parallel configuration to allow for the higher current requirements of a resistive-wire heating element 112. Further, for a resistive-gel version of the goggle 100, the batteries 114 could be employed in series configuration to allow for the higher voltage requirements of the resistive-gel heating element 112. Or, a combination of such wiring schemes could be applied to meet the demands of a particular system as will be understood by those of ordinary skill in the art of electronics design upon acquiring specific components for assembly of the goggle 100.

Opening of the power circuit by turning off the power switch 142, turns off the power to the heating element 112, thus rendering the anti-fog heating properties of the goggle 100 temporarily nonfunctional. Likewise, removal of the lens 104 from the goggle body 102 opens the circuit and disconnects the heating element from the heating source, thus rendering the anti-fog heating properties of the goggle temporarily nonfunctional. Similarly, use of a lens without a heating element 112 and without lens contacts 138, 140 also opens the circuit so as to render the anti-fog capability of the goggle 100 temporarily nonfunctional until an anti-fog enabled lens 104 is installed. Since it is an object of the invention to provide an anti-fog enabled and capable goggle with an easily interchangeable lens, the use of a lens not having an anti-fog heating element 112 with the goggle body 102 otherwise having the anti-fog electronics included nevertheless falls within the scope and spirit of the present invention.

Figure 8:
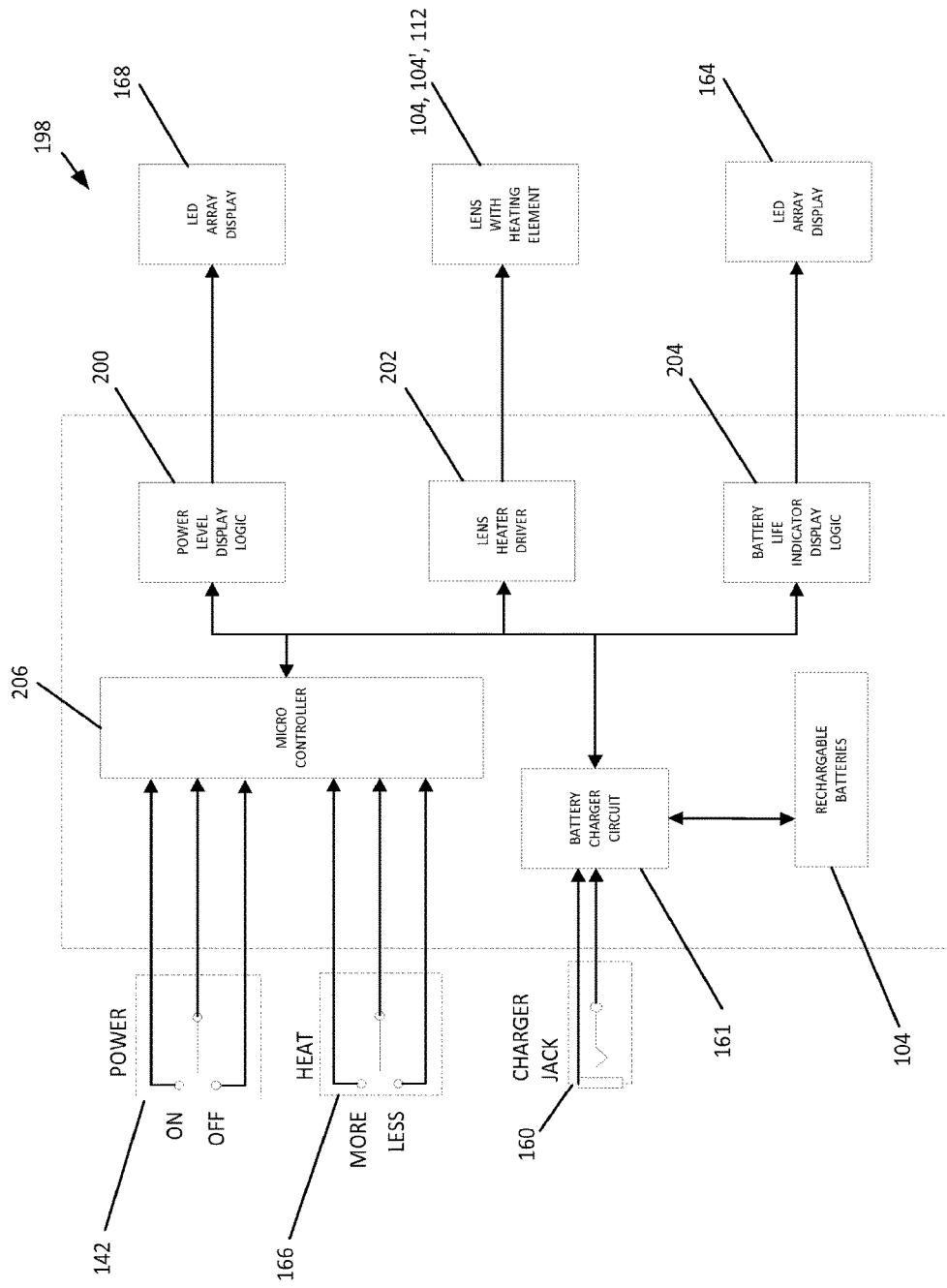
FIG. 8 is a schematic block diagram showing computing functions for a goggle in accordance with the present invention.

FIG. 8 shows a block diagram of the power and electronic system 198 of the goggle 100, 100'. The power and electronic system 198 is master-controlled by a microcontroller 206 and powered by rechargeable batteries 114 able to be recharged via a battery charger circuit 161 connected to a charger jack 160. Power to the system is switched on or off via a single-pole, dual throw, normally open, three-position, rocker switch 142 which is operatively connected to a micro-controller 206 to start or stop the functions of the goggle. A desired level of heat may be selected with the use of a single-pole, dual throw, normally open, three-position, rocker switch 166, which similarly is operatively connected with the micro-controller 206 for power adjustment of heat supplied the goggle. The LED array 164 for displaying battery life is controlled by battery life indicator display logic 204. The lens heating element 112 is controlled by a lens heater driver 202. The LED array 168 for displaying the heating power level applied to the heating element 112 is controlled by power level display logic 200.

Upon initiation of power to the goggle with switch 142, or upon initiation of a more power or less power signal from switch 166, the microcontroller 206, sends a corresponding signal to the lens heater driver to increase the voltage, or decrease the voltage provided to the heating element 112, which in turn increases, or decreases, the amount of heat which the heating element produces. At the same time as those adjustments are made, the microcontroller 206 sends a corresponding signal to the power level display logic 200 to turn on, or turn off, LEDs in the power level LED array display 168 in a manner that is representative of the level of power being applied to the lens 104. The system is calibrated such that when the maximum voltage is applied to the heating element 112, the most significant LED is turned on indicating maximum power. Conversely, when the least amount of voltage is sent to the heating element 112, the microcontroller 206 signals to the power level display logic 200 to turn on the least significant LED in the array display 168 indicating the power is nearly off. In either case the microcontroller 206 awaits for a pre-determined amount of time and then turns the LED array display 168 off to conserve power.

Any time the power switch 142 is depressed, in either on or off position, or the power level switch 166 is depressed, the microcontroller 206 requests from the battery charger circuit 161 an estimated recharge level available in the batteries and sends a corresponding signal to the battery life indicator display logic 204 to display the power level. Activation of the most significant LED of the array indicates full power and activation of the least significant LED of the array indicates minimal power available and that the batteries should be recharged soon. Of course, any number of LEDs could be in the array, and different colors of LEDs may be used to enhance the informational capabilities of the display.

Lens/Body Interconnection Means

Referring further specifically to FIGS. 3*a-d* and 5*a-c*, each lens 104 has a peripheral edge 107, a peripheral anterior surface 117 and a peripheral posterior surface 119 all around the outer periphery of the lens, and the goggle body 102 further comprises an inner peripheral engagement receptacle 150 around the inner periphery of the goggle body for receiving the lens within the body, the edge 107 and anterior surface 117 engaging with the receptacle 150 on and around peripheral edge 107 and on the anterior edge surface 117 of the lens 104. Posterior of the engagement receptacle 150, the goggle body 102 further comprises a portion of a mated retention means 152 attached or defined around the inner periphery of the body. Preferably, this portion of mated retention means 152 comprises a groove 152 defined in the inner periphery of the body 102. The posterior face contact 101 further comprises a removable lens retaining, or interface, member 154 adapted for engaging the posterior edge portion 119 of the lens 104, the removable lens retaining member 154 being glued or otherwise attached to the preferably foam rubber face contact 101. The removable lens retaining member 154 preferably comprises a semi-rigid plastic frame member 154 which carries the other portion 156 of the mated retention means around the periphery, the other portion comprising a tongue 156 formed around the periphery of the semi-rigid plastic lens retaining member. The removable lens retaining member 154, and its tongue 156, is for releasably interconnecting with the portion of the mated retention means 152 around the inner periphery of the body 102 for retaining the lens 104 within the receptacle 150 of the goggle body.

Once the lens 104 has been placed in the receptacle 150 of the goggle body adapted to be a distance from the user's eyes upon user installation of the goggle, and so as to provide a shield for the eyes, the face contact 101 and integral or attached interface member 154 are snapped into place behind, or posterior of, the lens, contacting and engaging an anterior peripheral surface 158 of the interface member 154 with the posterior peripheral surface 119 of the lens 104 for holding the lens in place and such that the lens contacts 138, 140 are held in place in electrical contact with the corresponding body contacts 139, 141. The tongue 156 and groove 152 are designed to be a snap, or force, fit such that there is required a small force to overcome the interconnection between the two once the lens 104 is installed in the receptacle 150 of the goggle body 102.

Figure 2:
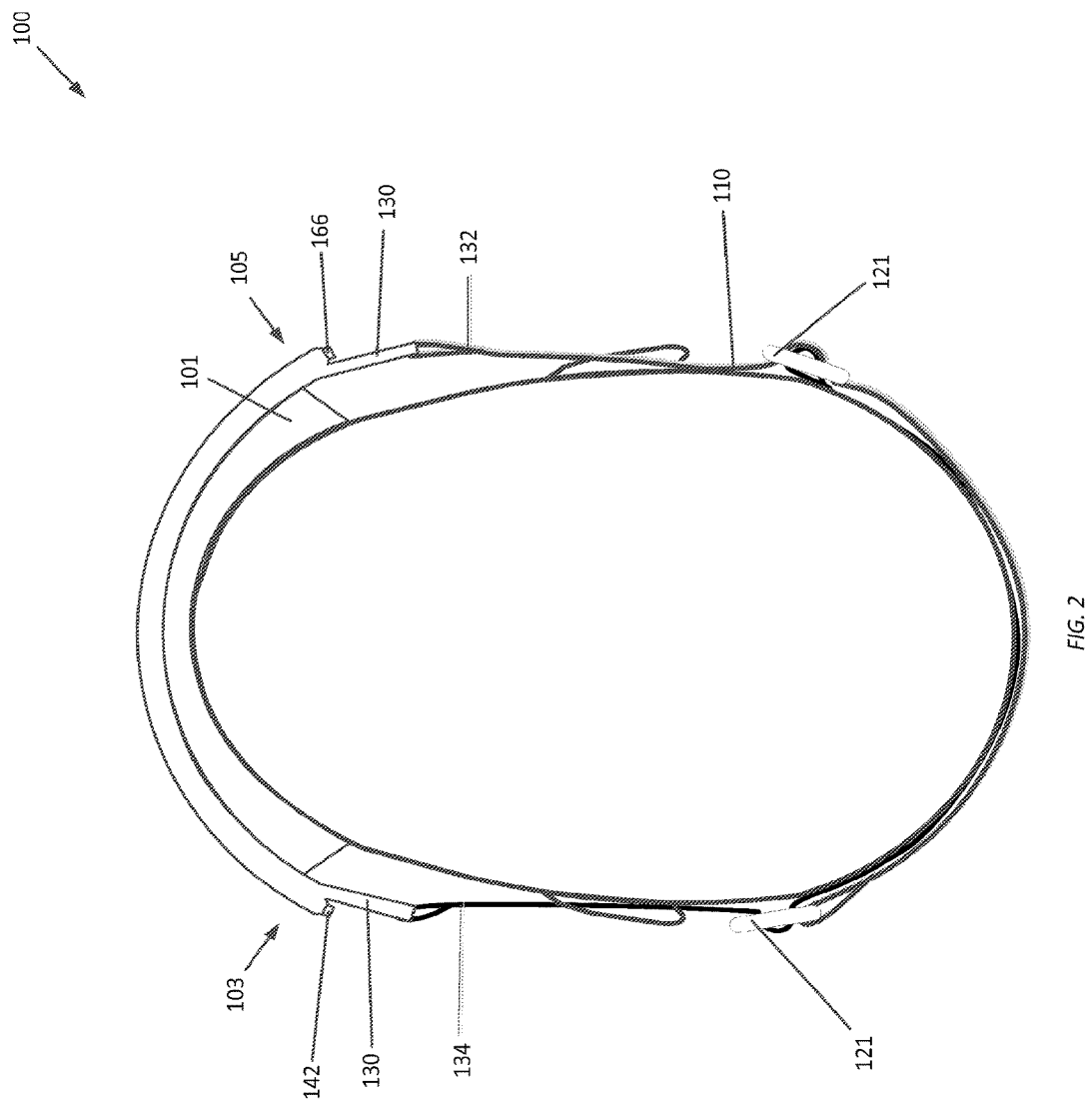
FIG. 2 is a top plan view of a goggle in accordance with the invention and shown strapped on a user's head.
Figure 5A:
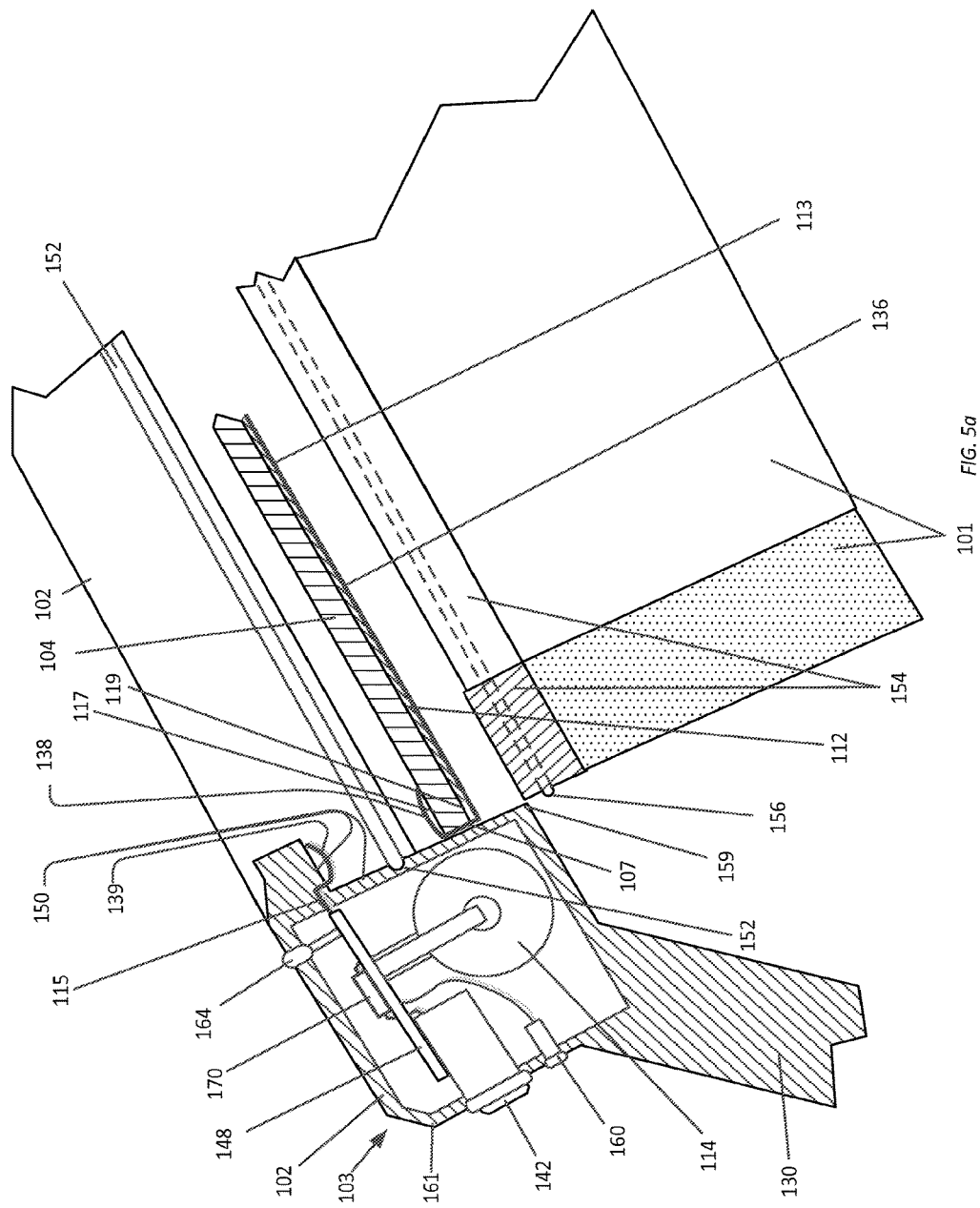
FIG. 5a is a detailed cross-section partial top view showing parts of an anterior goggle body with internal battery and electronics, an anti-fog lens, and a posterior lens retainer/face contact member combination of a goggle prior to installation of the lens and lens retainer/face contact member in the body in accordance with the first embodiment of the invention.
Figure 5B:
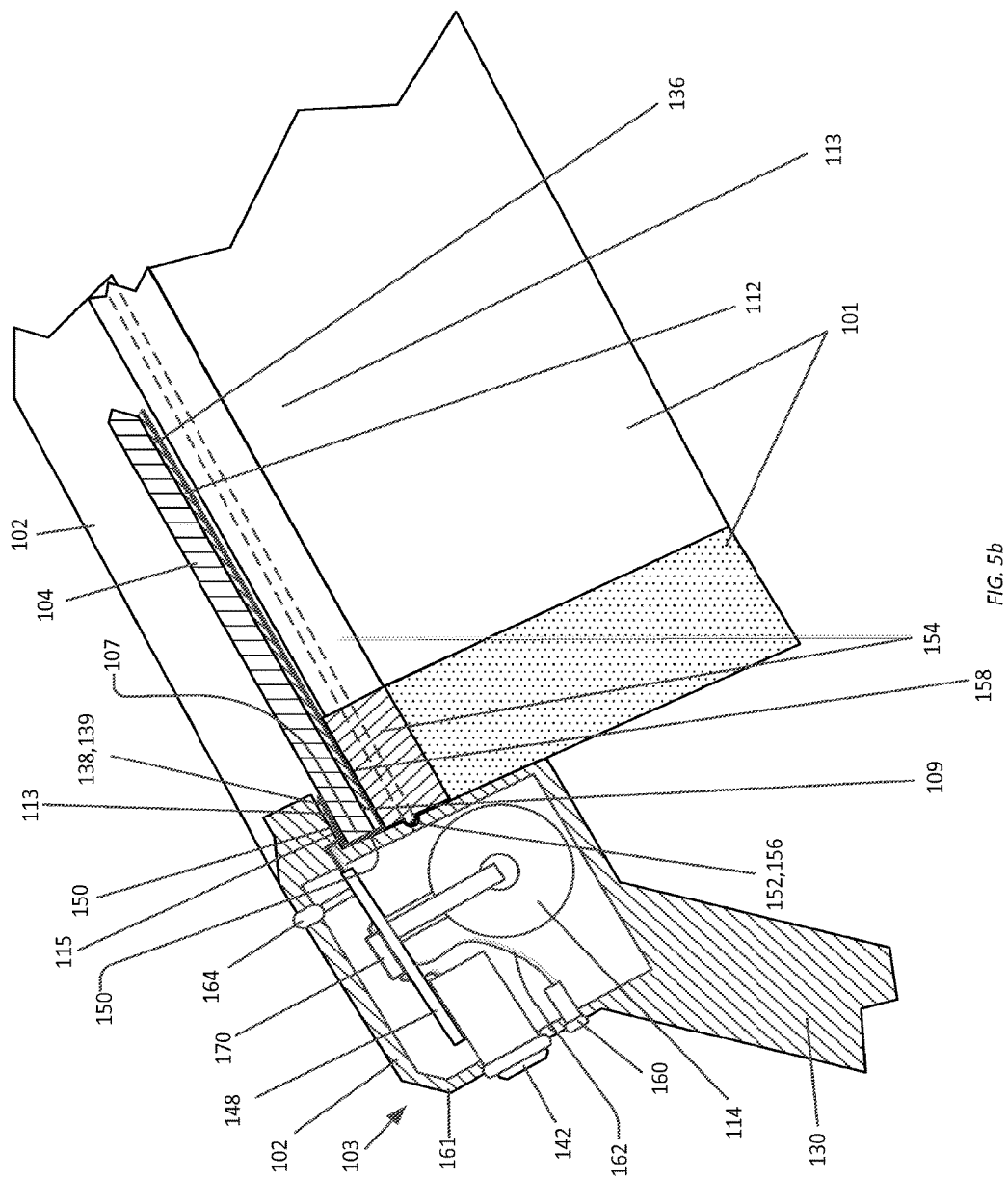
FIG. 5b is a detailed cross-section partial top view showing the parts of a goggle in accordance with the first embodiment of the invention and after installation of the lens and lens retainer/face contact member combination in the body showing contact of the resistive lens heating element with the battery.

FIG. 5*a* shows the left side 103 of the goggle body 102, lens 104 and posterior face contact 101/interface lens retaining member 154 prior to installation of the lens and the posterior face contact/interface lens retaining member as described. FIG. 5*b* shows the left side 103 of the goggle body 102 after installation of the lens 104 and posterior face contact 101/interface lens retaining member 154, with tongue 156 installed into groove 152, the goggle 100 now being ready for placement on a user's head as shown in FIG. 2. Further, it will be appreciated that strap 110 attached to strap attachment members 130 serve not only to retain the goggle 100 on the user's head, but to help maintain the tongue 156 in the groove 152 during wear, and hence, positive contact between the lens contacts 138, 140 and the body contacts 139, 141.

Figure 5C:
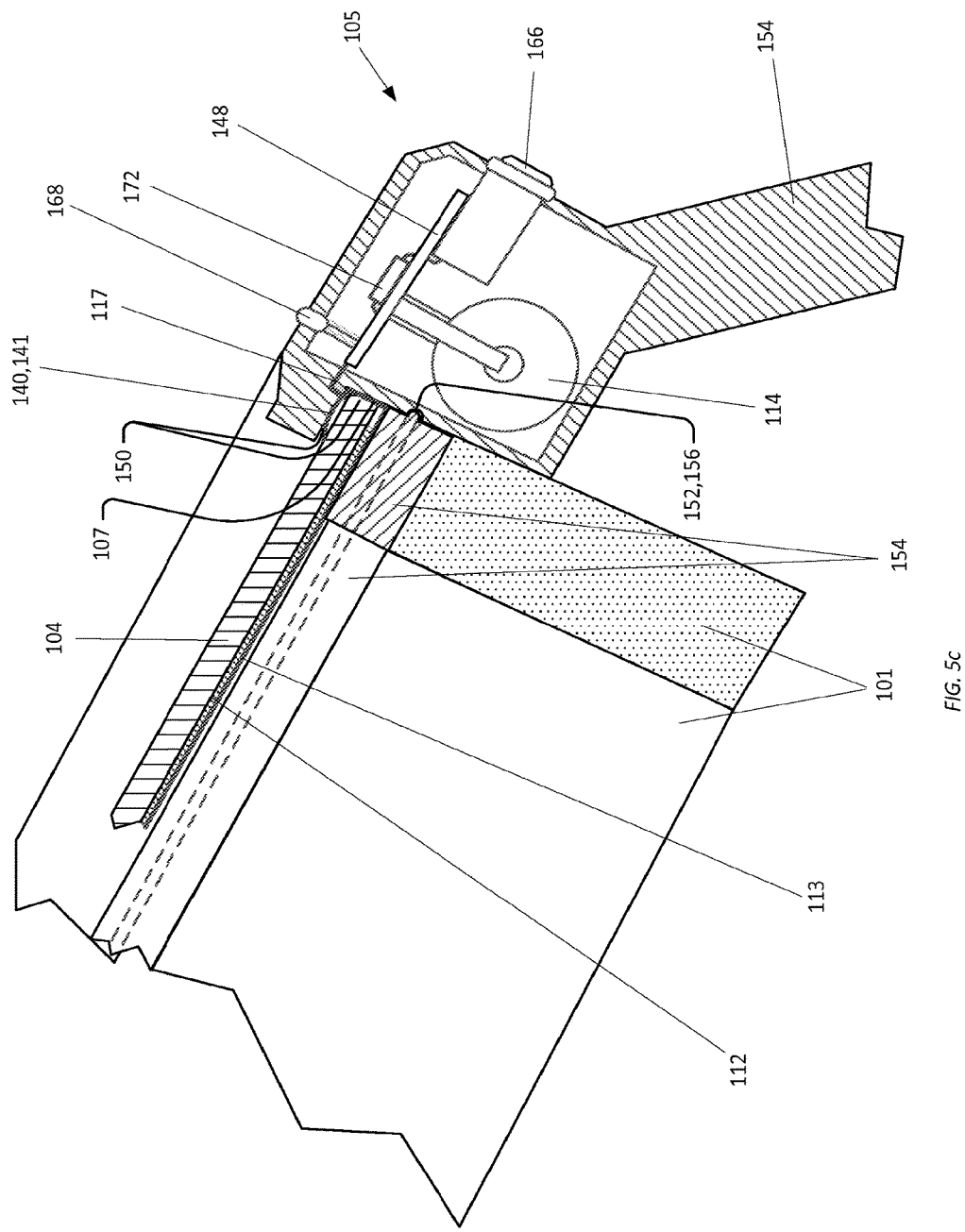
FIG. 5c is a detailed cross-section partial top view showing another end of the goggle of FIG. 5a after installation of the lens and lens retainer/face contact member combination in the body showing contact of another end of the resistive lens heating element with the battery.

Referring specifically to FIG. 5c, the right side 105 of the goggle 100 is shown, with the lens 104 having heating element 112 thereon and being retained in receptacle 150 in the goggle body 102 by removable face contact 101/interface lens retaining member 154, together with tongue 156 and groove 152 shown engaged, the tongue and groove extending around the entire periphery of the lens retaining member and the inner periphery of the body respectively.

Interchangeable Lenses

Referring now to FIGS. 3a-d, there are shown front plan views of interchangeable lens portions 104 and a front plan view of the corresponding face contact portion 101/lens interconnection frame member 154 described above, for use in accordance with the first embodiment of the invention and showing that the tongue 156 preferably extends around the entire periphery of the lens interconnection frame member 154.

Figure 3A:
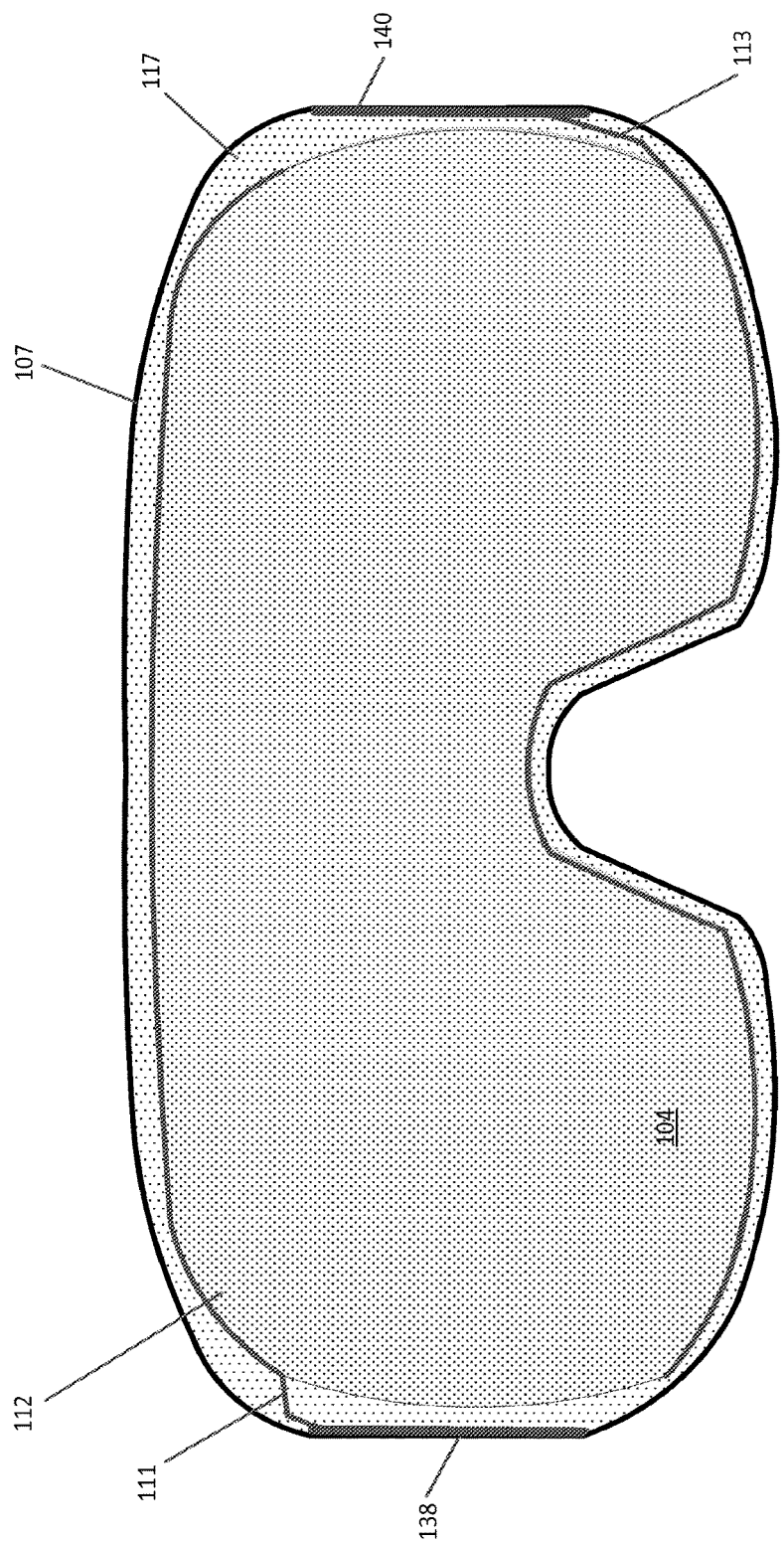
FIG. 3a is a front plan view of a tinted, anti-fog lens of a goggle in accordance with a first embodiment of the invention, the lens having resistive-gel anti-fog means thereon.

FIG. 3a shows a lightly tinted lens portion 104 of a goggle 100 and having resistive-gel anti-fog means 112 thereon. The lens 104 has buss bar wires 111, 113 interconnecting the gel anti-fog means 112 with lens contacts 138, 140, respectively. The peripheral edge 107 and the peripheral anterior surface of the lens 104 are adapted for retention within the receptacle 150 of the goggle body 102, where the lens contacts 138, 140 interconnect with the corresponding body contacts 139, 141. The lens 104 is held into place in the receptacle 150 with the assistance of the lens interconnection frame member 154 shown in FIGS. 3d and 5a-c.

Figure 3B:
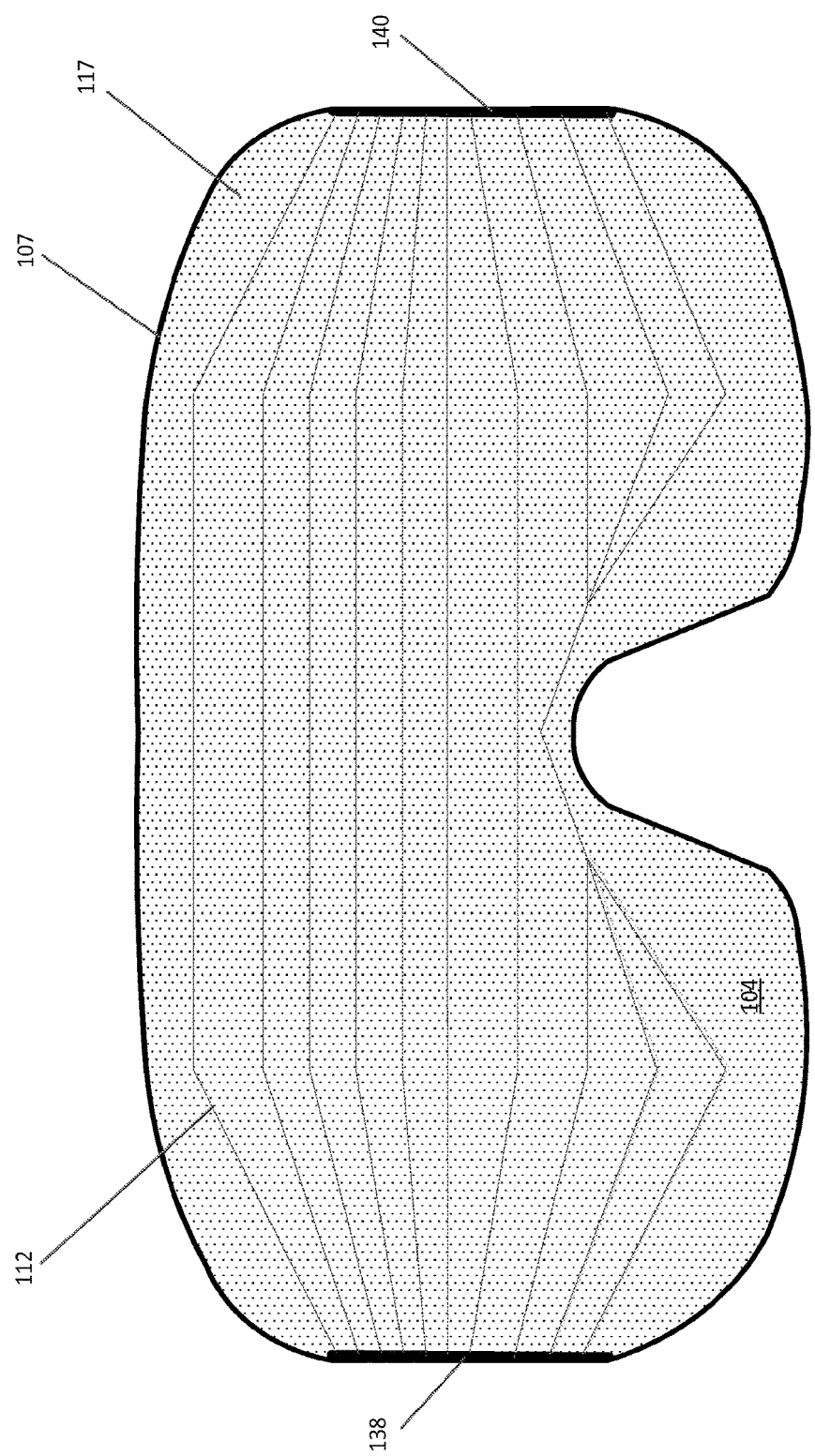
FIG. 3b is a front plan view of an alternate, differently-tinted, anti-fog lens of a goggle in accordance with the first embodiment of the invention, the lens having resistive-wire anti-fog means thereon.

FIG. 3b shows an alternate shade tinted lens portion 104 of a goggle in accordance with the invention and having resistive-wire anti-fog means 112 thereon. The wires of the resistive-wire anti-fog means 112 of the lens 104 of FIG. 3b are interconnected by contacts 138, 140. The peripheral edge 107 and anterior peripheral surface 117 of the lens 104 of FIG. 3b are likewise adapted for engagement within the receptacle of the goggle body 102, where the lens contacts 138, 140 contact with the corresponding body contacts 139, 141. The lens 104 of FIG. 3b is likewise held into place in the receptacle 150 with the assistance of the lens interconnection frame member 154 shown in FIGS. 3d and 5a-c.

Figure 3C:
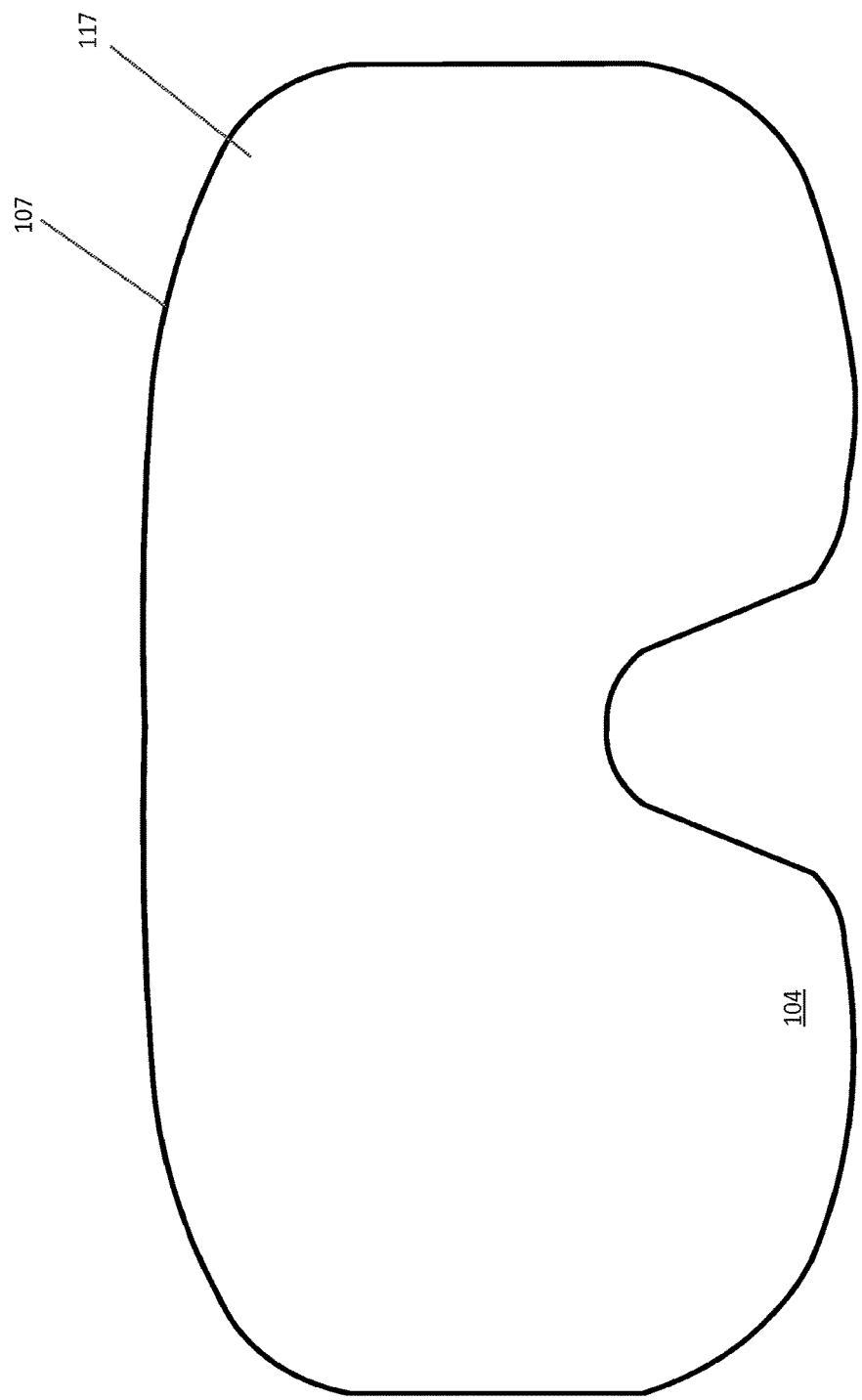
FIG. 3c is a front plan view of another alternate, non-tinted, lens of a goggle in accordance with the first embodiment of the invention, the lens having no anti-fog means thereon.

FIG. 3c shows another alternate lens 104 without any tint and without any anti-fog means or related electrical contacts thereon. The peripheral edge 107 and peripheral anterior surface 117 of this lens is likewise adapted for engagement and retention within the receptacle 150 of body 102 of the goggle 100 with the assistance of lens interconnection frame member 154 as shown in FIGS. 3d and 5a-c.

Figure 3D:
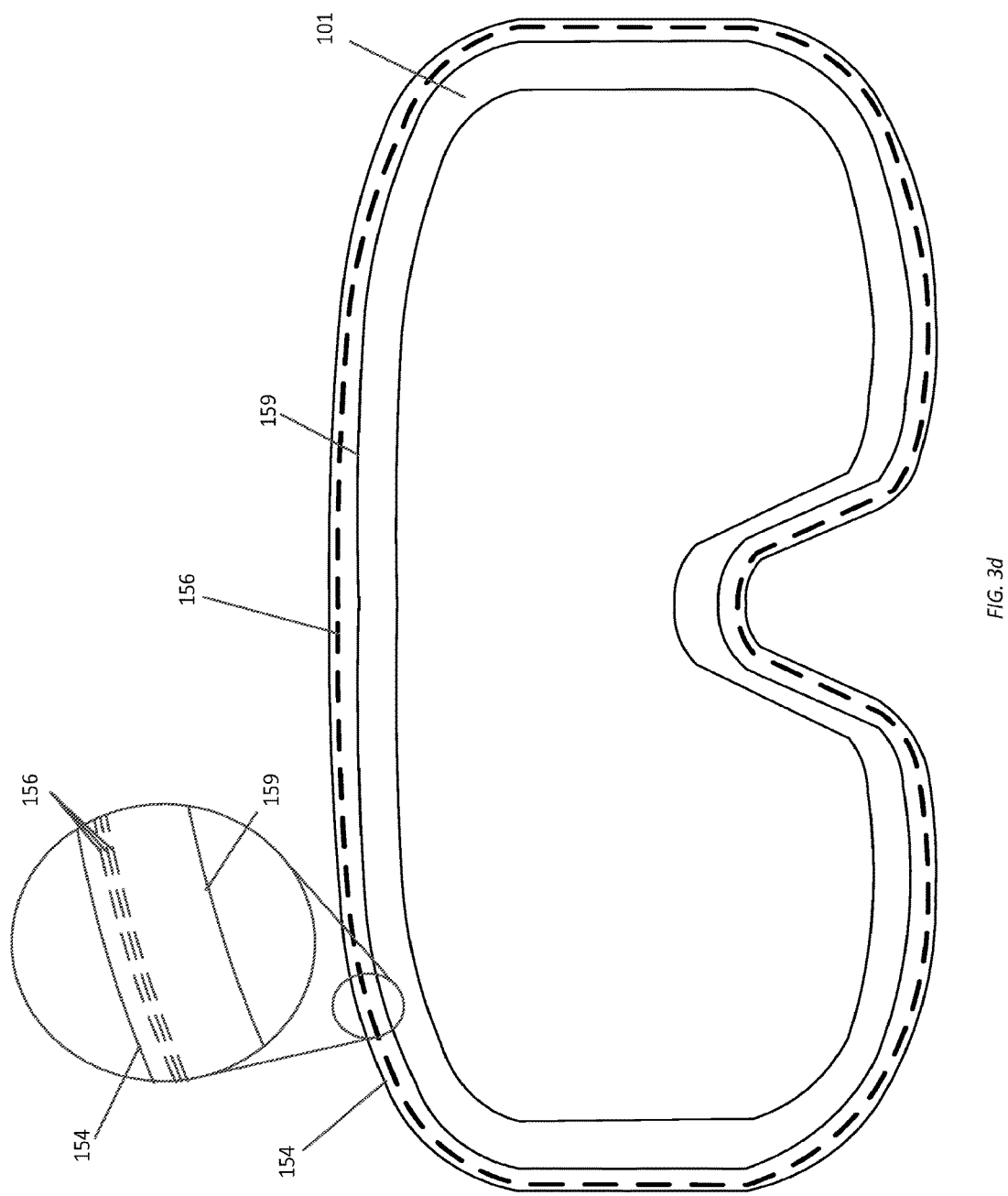
FIG. 3d is front plan view of a lens retaining/face contact member combination of a goggle in accordance with a first embodiment of the invention, the view also comprising a blown up portion to show further detail of the retaining member interconnection portion in accordance with a first embodiment of the invention.

Referring specifically to FIG. 3d, a front plan view of the face contact 101/lens retaining interface member 154 is shown comprising a tongue member 156 extending around the periphery of the interface member 154. The tongue 156 is adapted for receipt in a groove 152 defined around the inner periphery of the goggle body 102. The interior periphery of the goggle body 102 is angled slightly inwardly, similar to a funnel configuration, so that the face contact 101/lens retaining interface member 154 is guided into place to where it rests with tongue 156 retained in the groove 152 behind the lens 104. The tongue member 156 is part of the interconnection means for retaining the lens 104 in the lens retaining receptacle 150 of the goggle body 102. Posterior of the interface member 154 and around the periphery of the interface member, there is attached a face contact member 101, preferably comprised of foam rubber, for making a seal against the user's face, and that is glued, or otherwise attached, to the posterior portion of the interface member.

FIG. 3d further shows a magnified detailed portion of the interface member 154 and tongue 156, the tongue being represented by three dashed lines, one line for each side of the base of the tongue and one line for the ultimate tip of the tongue. Further, these three lines are represented as a single line extending around the periphery of the interface member 154 demonstrating that the tongue 156 preferably extends around the entire periphery of the interface member. It will be appreciated that, because of the somewhat irregular curvature of the interface member 154/face contact member 101 to adapt to the contours of a person's face, as is commonly understood in the goggle art, the lines representing the tongue 156 are for illustrative purposes, and the lines illustrating the tongue would at various points around the interface member be hidden by other lines for leading front edges of the interface member.

Figure 6A:
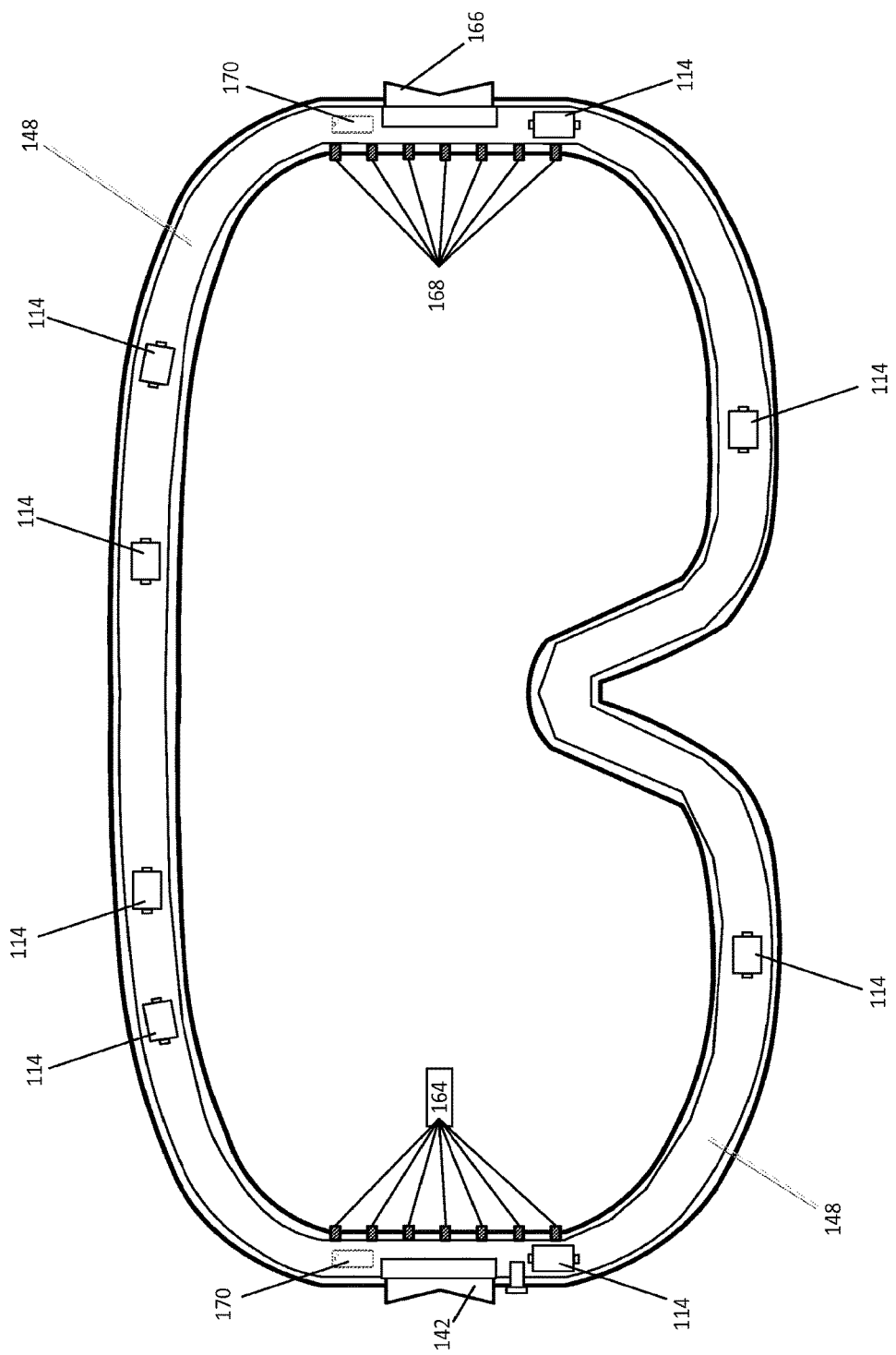
FIG. 6a is a rear perspective view of inside the body portion of a goggle in accordance with the present invention showing a flexible circuit board having thereon a heat level adjustment switch and heat level indicator diodes on one end of the goggle and an on/off switch and battery-level indicator diodes on another end of the goggle.
Figure 6B:
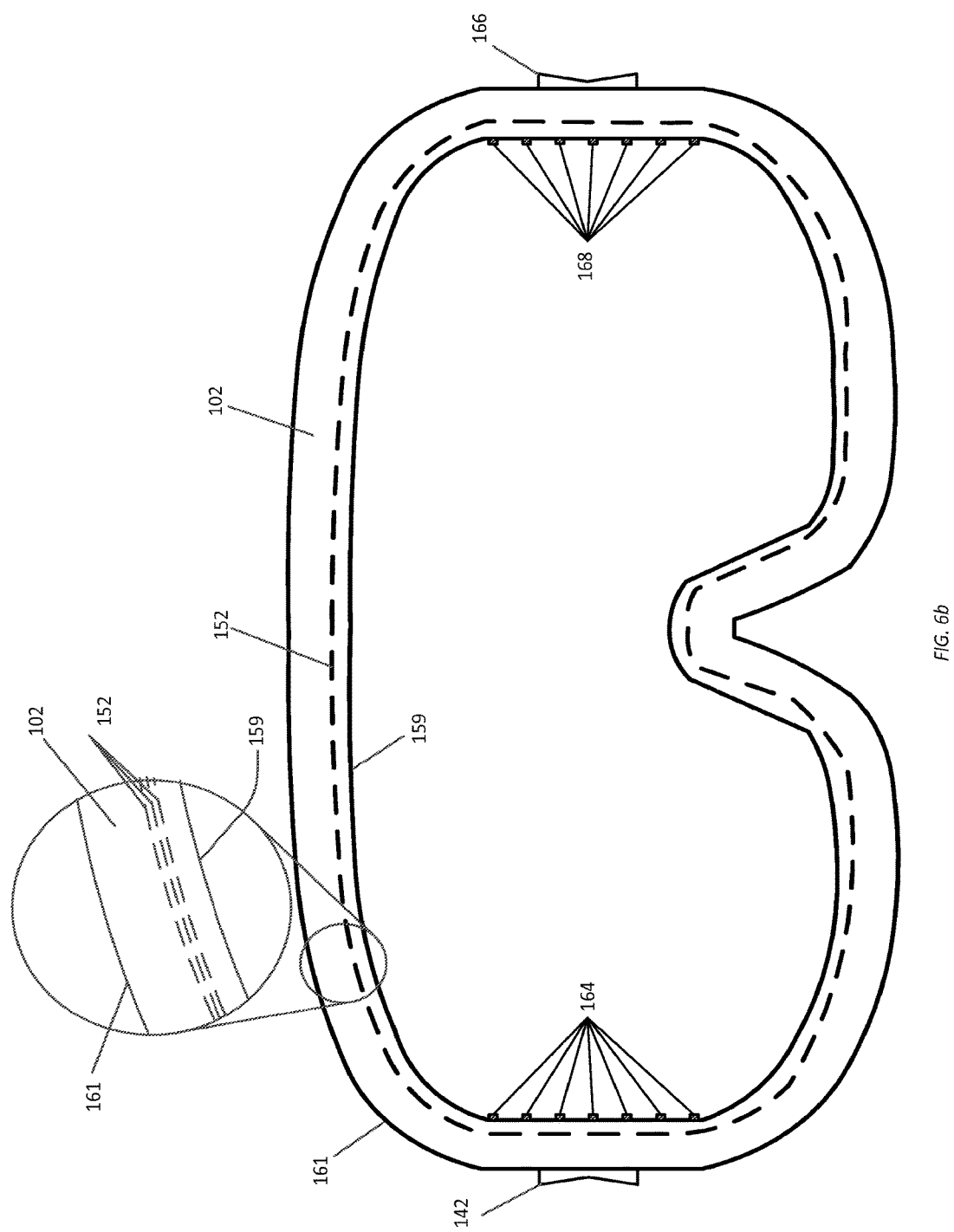
FIG. 6b is a rear perspective view of a portion of the goggle body in accordance with the first embodiment of the invention.

Referring now to FIG. 6b, showing a back view of the goggle body 102 (normal to the orientation of FIG. 5a), the groove 152 is shown as being defined around the entire inner periphery of the body. FIG. 6b also includes a magnified detailed portion of the groove 152 wherein the groove is represented by three dashed lines, whereas the groove as it extends around the remainder of the inner periphery of the goggle body 102 is represented as a single dashed line for sake of illustration and because three dashed lines would be too close together to distinguish in the drawing. For added reference and understanding of the drawing, reference points 159 and 161 correspond to like reference points, or edges, on FIG. 5a. Other hidden lines are left off of drawing 6c for sake of clarity.

This aspect of the invention provides for easy interchangeability of differing tinted lenses 104 having anti-fog means 112 thereon, since, upon removal of the goggle from the user's head, the face contact 101/retaining member 154 is able to be grabbed and removed from its interconnected engagement with the body 102. This feature makes use of the goggle 100 more care-free, as whether the goggle is switched on, or off, the user is encouraged in choosing a goggle that suits the weather, terrain, and lighting conditions of the moment. Removal of the retaining member 154 may be facilitated by flexing the goggle body 102 and lens 104 combination in opposition to the natural curvature of the lens and goggle body to pop the seal between the tongue 156 of the retaining member and the groove 152 of the body 102. Alternatively, a small pull tab or zip cord (not shown) may be added to the rear side of the retaining member 154 for facilitating and directing grabbing and removal of the face contact 101/retaining member 154 combination.

Resistive-Wire Heating Element Version

In FIG. 3b, the heating element 112 is shown as a resistive-wire heating element preferably sandwiched with transparent glue between two lenses comprising a composite lens 104 as is known in the art. The resistive-wire heating element 112 branches from contacts 138, 140 with the contacts leading, upon installation of the lens 104 into the goggle body 102, to and from power control circuitry on the flexible circuit 148 as described previously.

Resistive-Gel Heating Element Version

In FIG. 3a, the heating element 112 is shown as a resistive-gel heating element with buss bar lead wires 111, 113 leading to and from the resistive-gel heating element and in contact with lens contacts 138, 140 that, upon installation of the lens 104 in the goggle body 102, connect with corresponding goggle body contacts 139, 141, as described above, to interconnect the resistive-gel heating element with the flexible circuit board 148 and power circuit described previously.

As is known in the art, the gel heating element 112 comprises a transparent conductive oxide heating element along with metal, such as silver, buss bar lead wires 111, 113, both of which are deposited on the lens 104 via DC magnetron sputtering process, ion-enhanced E-beam vaporization process, or pressure-sensitive adhesive laminate onto a semi-rigid optical substrate, such as acrylic or polycarbonate, of the lens 104.

It will be appreciated that the basic configuration of the power electronics shown in FIGS. 5a-c and 6-8 apply whether the resistive-gel version of the lens 104 is utilized or the resistive-wire version of the lens 104 is utilized, though there would be some differences in the circuitry for one version over the other as will be apparent to those of ordinary skill in the art upon learning manufacturer specified power requirements for either type of heating element.

Other Goggle Electronic Features

Figure 6C:
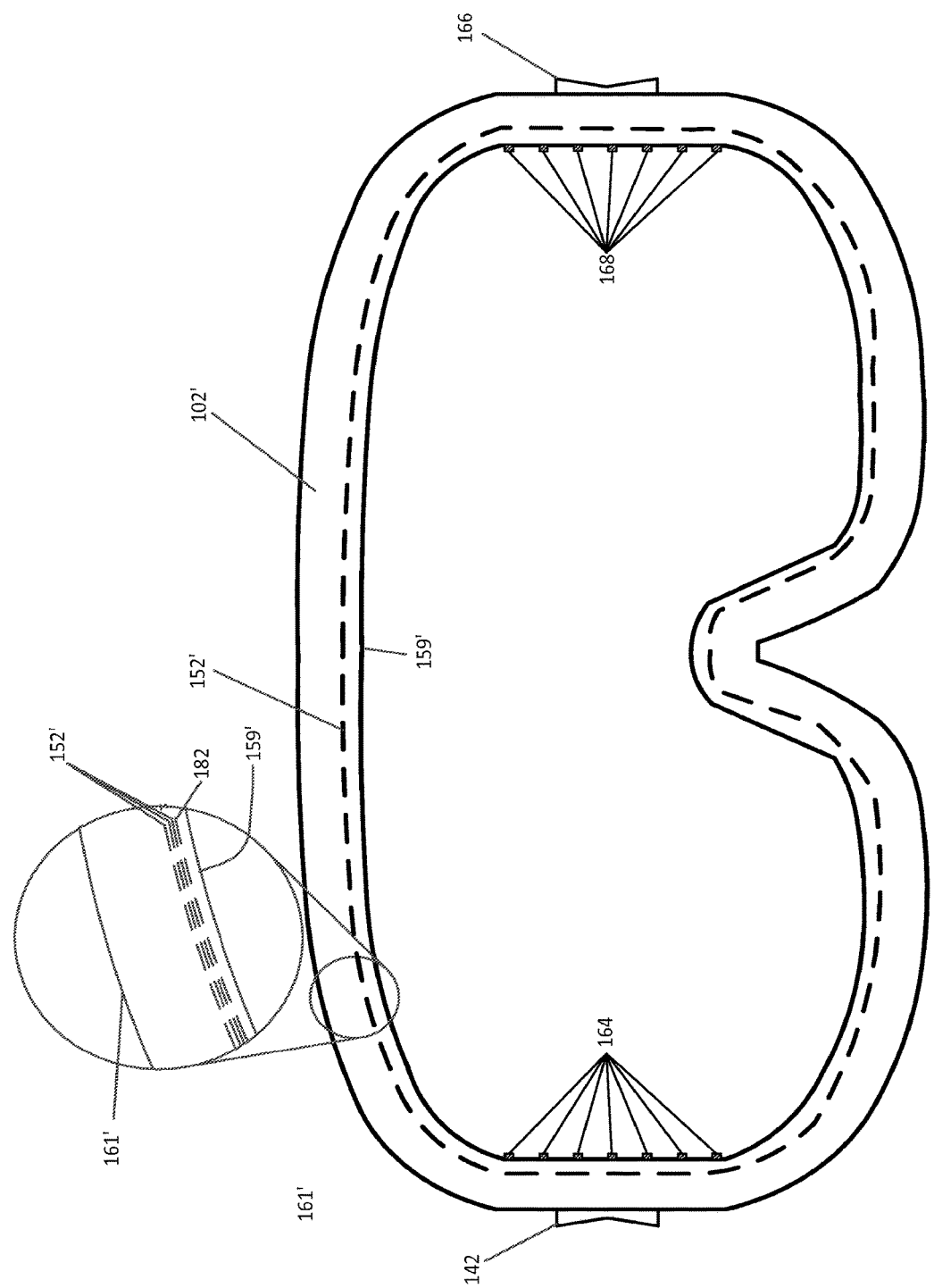
FIG. 6c is a rear perspective view of a portion of the goggle body in accordance with the second embodiment of the invention.
Figure 7:
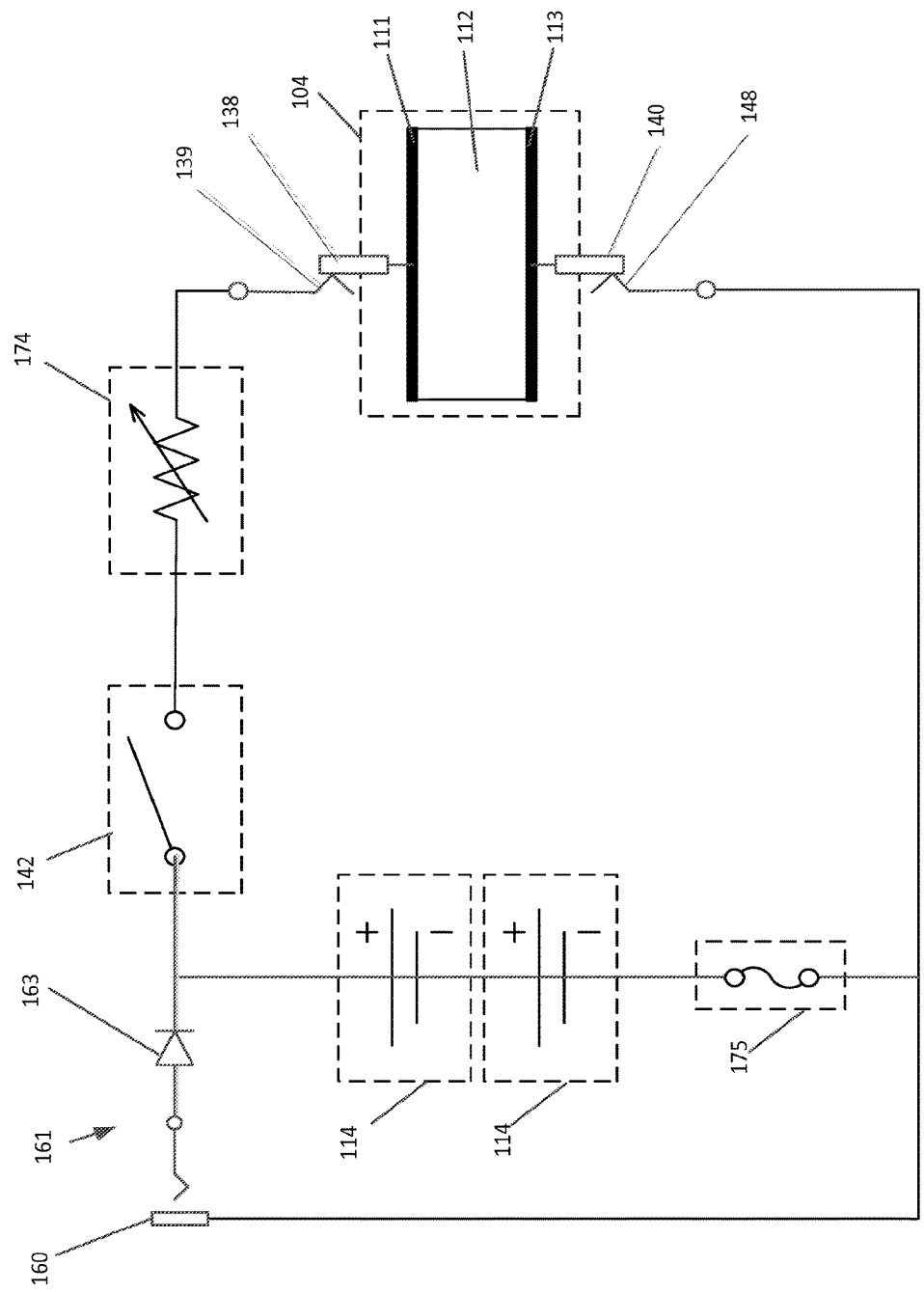
FIG. 7 is a schematic diagram showing circuitry for a goggle in accordance with the present invention.

Referring further to FIGS. 5a-b and 6-8, there is shown a charging jack 160 and connecting wire 162 for allowing recharging of the batteries 114 of the goggle 100. Referring specifically to FIG. 7, in addition to the charging jack 160, there is shown a charging circuit 161 comprising the battery jack 160 and a diode 163 in series with the batteries 114. When a charger is plugged into the jack 160, current flows through the jack to refresh the batteries 114. The diode 163 prevents the battery charger from inadvertently discharging the batteries 114 should the charger not produce any current as when it is unplugged or there is a short circuit. Of course, it will be appreciated that other means of recharging the batteries 114 may be employed, including a charging mat (not shown) as is known in the art.

The goggle 100 further comprises a plurality of LED indicators in an LED array 164, as further shown in FIGS. 1 and 6, depending from the flexible circuit 148. Upon turning on the power to the goggle 100 with the power switch 142, and also upon re-activating the on position of the power rocker switch, the LED array 164 turns on temporarily to show that the power is on and battery strength, the more LEDs that light up, the more battery life that is remaining.

Referring further to FIGS. 5c, 6a, and 7-8, the goggle 100 further comprises a power heat adjustment and indicator switch 166 operatively connected with a variable resistance voltage control circuit 174 and another LED array 168, for user feedback and selection of the amount of anti-fog power to be applied to the heating element 112 of the goggle 100, the more LEDs lighting up, the more power that is being applied to the anti-fog heating element 112 of the lens 104 at a given time.

The switches 142 and 166 are preferably rocker switches that are easy to operate, even with a gloved hand, while the goggle 100 is being worn, and lights from the LED arrays 164, 166 are able to be seen temporarily by the user from inside the goggle, since the LED arrays wrap around from the side of the goggle into the user's visible field of vision.

The lens 104 of the goggle in accordance with this embodiment of the invention need not be used as an anti-fog lens, either because power to the lens may be turned off, or because there is no anti-fog element on the particular lens chosen. Nevertheless, such a goggle 100 does not depart from the true scope and spirit of the invention as claimed herein, since the power to the lens may be turned on with the power switch 142, or another lens with an anti-fog element 112 thereon may be easily substituted for a current lens not having an anti-fog element thereon.

Combined Lens and Lens Retention Member Embodiment

Referring specifically now to FIGS. 3e-g and 5d-f, an alternate embodiment of the lens 104' is shown wherein the lens further comprises an attached, or integrated, face contact 101'/lens retaining member 154'. Thus, a primary difference between this embodiment of the invention and the first embodiment of the invention is that the lens 104 of the first embodiment of the invention is a separate module from the face contact 101/lens retaining member 154, whereas with this embodiment of the invention, they are more permanently attached, or are of integrated construction. Attachment of the tongue 156' of the engagement or interconnection means to any of the lens portions 104' of FIGS. 3e-g and 5d-f is accomplished through injection molding of the lens retaining member 154' and subsequent gluing, pressure or snap fit retention and/or other physical attachment means between the lens and the retaining member. The tongue 156' is preferably integrally formed with the retaining member 154' or molded around the entire periphery of the retaining member in durable fashion.

Figure 5D:
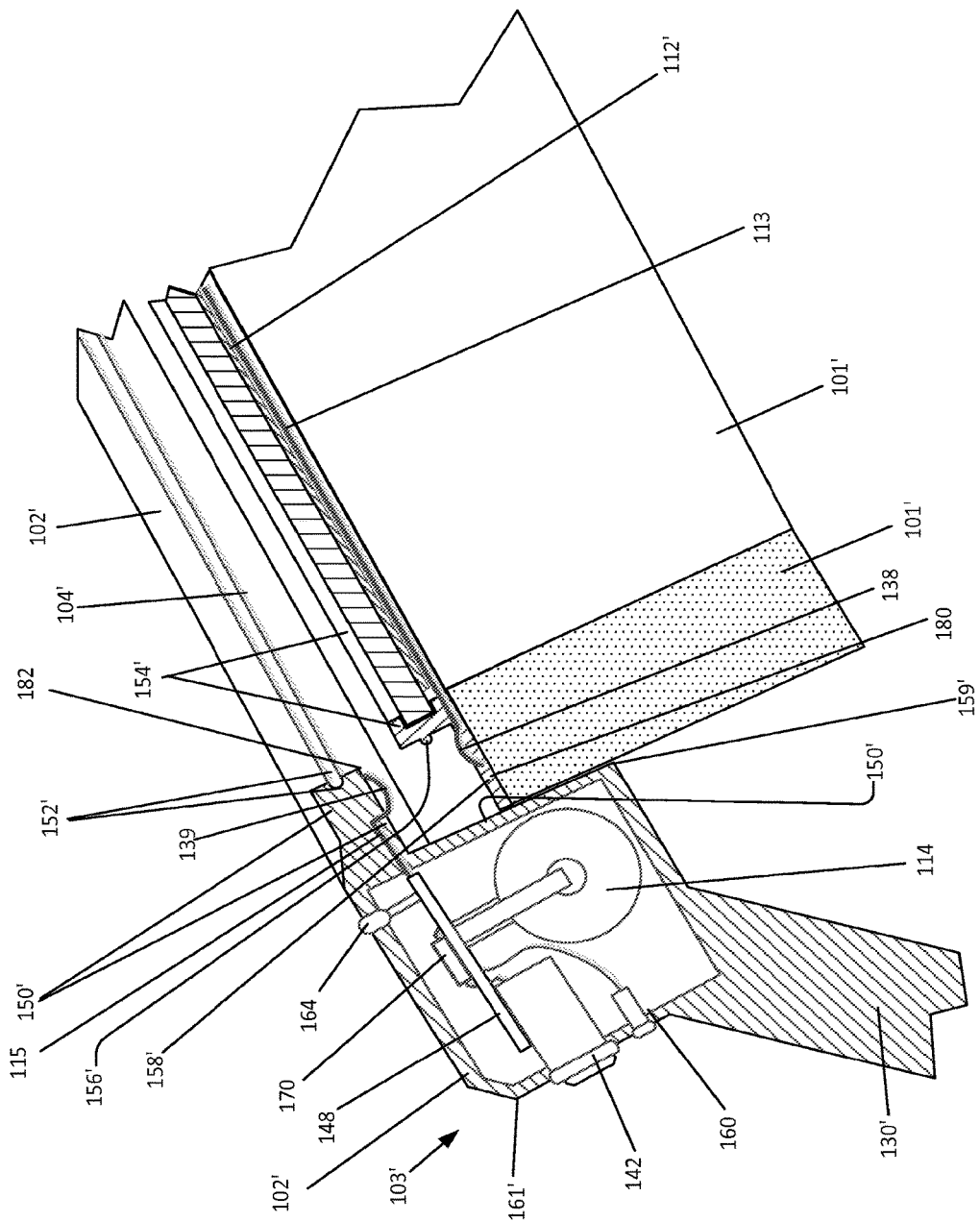
FIG. 5d is a detailed cross-section partial top view showing parts of an anterior goggle body with internal battery and electronics, an anti-fog lens/lens retainer/face contact member combination of a goggle prior to installation of the lens/lens retainer/face contact member combination in the body in accordance with the second embodiment of the invention.
Figure 5E:
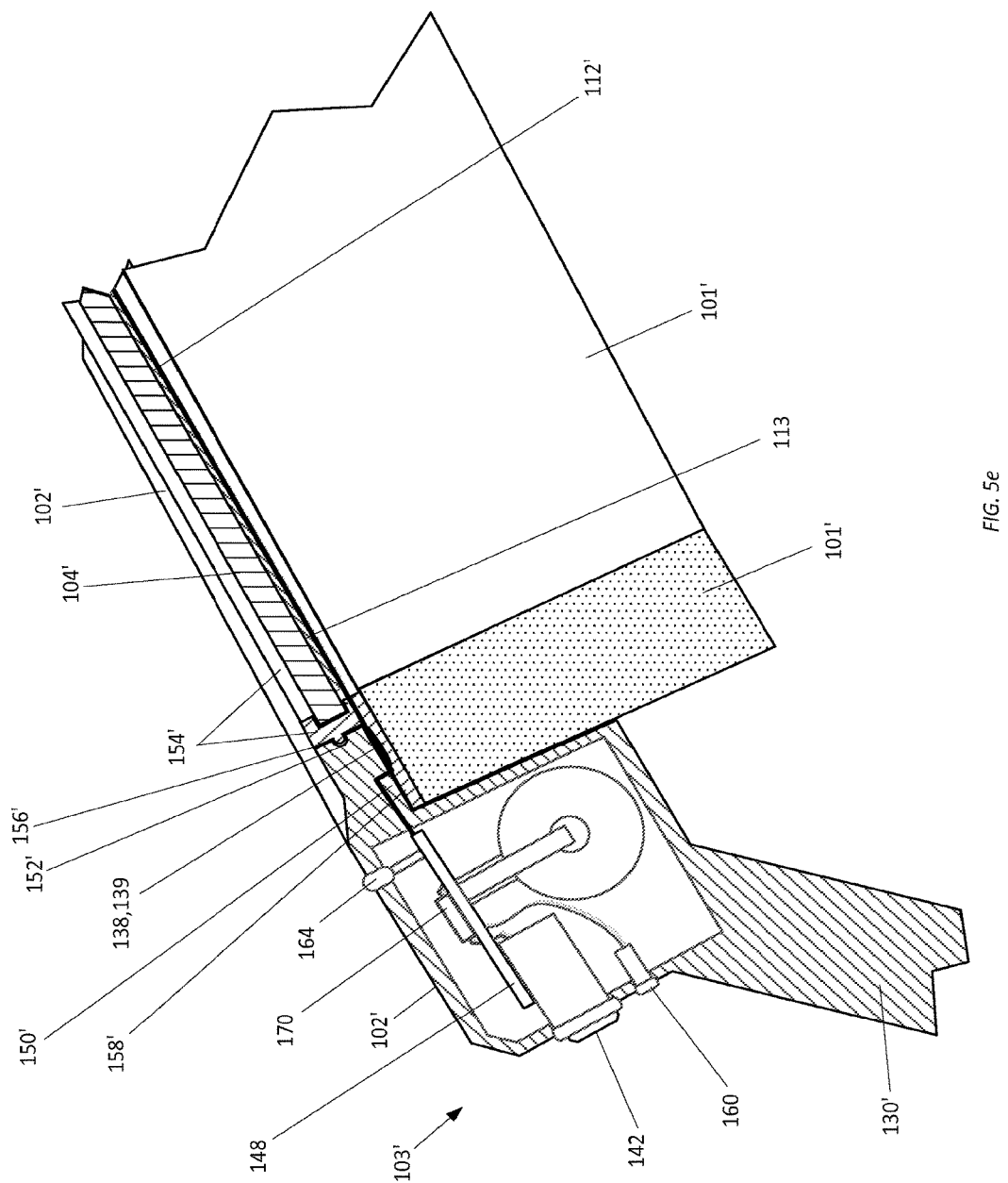
FIG. 5e is a detailed cross-section partial top view showing the parts of a goggle in accordance with the second embodiment of the invention and after installation of the lens/retainer/face contact member combination in the body showing contact of the resistive lens heating element with the battery.

FIG. 5d shows the left side 103' of the goggle body 102' and combined lens 104'/posterior face contact 101'/lens retaining member 154' prior to installation of the combination lens/face contact/interface lens retaining member as described. FIG. 5e shows the left side 103' of the goggle body 102' after installation of the combined lens 104'/face contact 101'/lens retaining member 154', with the tongue 156' installed into the groove 152', the goggle 100' now being ready for placement on a user's head as shown in FIG. 2. Further, as described above in connection with FIG. 2, it will be appreciated that with this embodiment of the invention, as with the first embodiment of the invention, a strap 110 attached to strap attachment members 130 serve not only to retain the goggle 100' on the user's head, but to help maintain the tongue 156' in the groove 152' during wear, and hence, positive contact between the lens contacts 138', 140' and the body contacts 139', 141'.

Figure 5F:
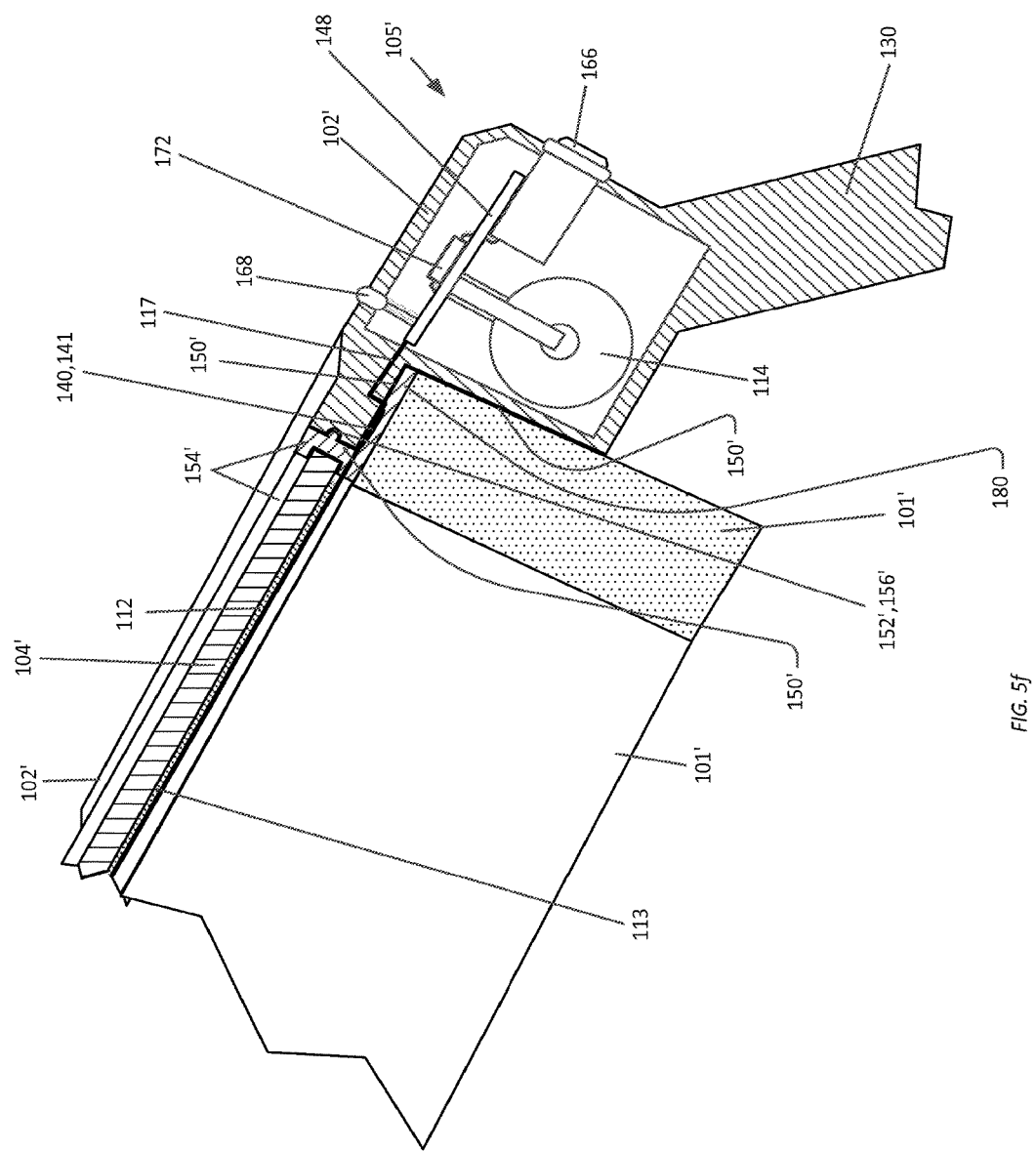
FIG. 5f is a detailed cross-section partial top view showing another end of the goggle of FIG. 5d after installation of the lens and retainer/face contact member combination in the body showing contact of another end of the resistive lens heating element with the battery.

Referring specifically to FIG. 5f, the right side 105' of the goggle 100' is shown, with the lens 104' having heating element 112' thereon. The combination lens 104'/retaining interface member 154'/face contact 101' is shown being retained in receptacle 150' in the goggle body 102' with tongue 156' seated in groove 152', shown engaged in FIG. 5f, the combination lens/retaining interface member/face contact having been installed into the goggle body. Further, as with the previously described embodiment of the invention, the tongue 156' and groove 152' extend around the entire periphery of the lens retaining interface member 154' and the inner periphery of the body 102', respectively.

Referring to FIGS. 5d-f, there are provided lens contacts 138', 140' in the lens retaining member 154', the lens contacts being in electrical contact with the heating element 112' of the lens 104'. Corresponding body contacts 139', 141' are found in the receptacle 150' of the goggle body 102', the body contacts being electrically connected with the flexible circuit board 148', and hence battery 114', power switch 142', power level adjustment switch 166', and IC control chips 170', 172' by wires 115', 117' as shown. Similarly as described in connection with the primary embodiment of the invention, there are provided LED arrays 164' and 166' for indicating battery-life and power level.

Interchangeable Lenses

Figure 3E:
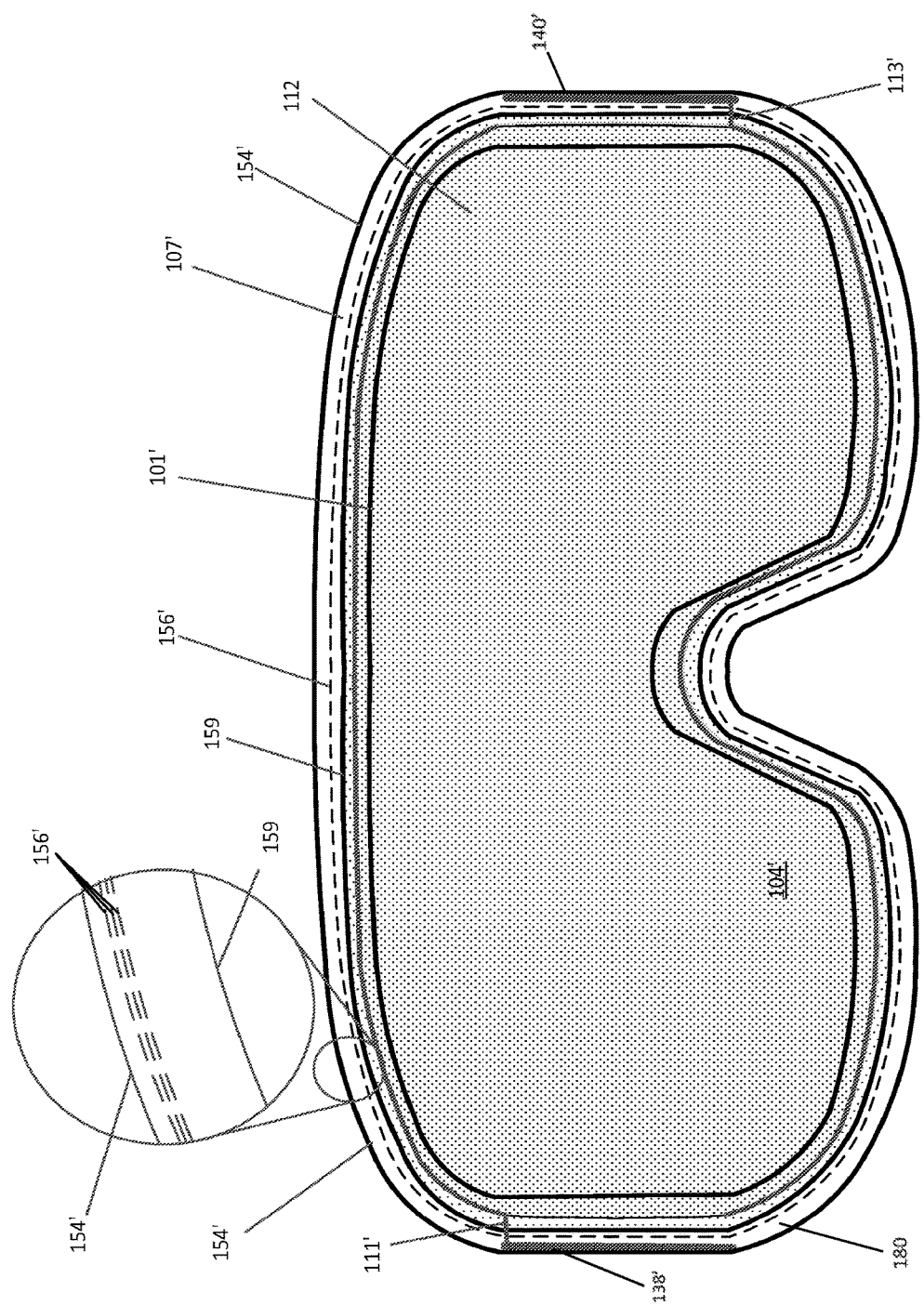
FIG. 3e is a front plan view of a tinted, anti-fog lens/retaining/face contact member combination of a goggle in accordance with a second embodiment of the invention, the lens having resistive-gel anti-fog means thereon.
Figure 3F:
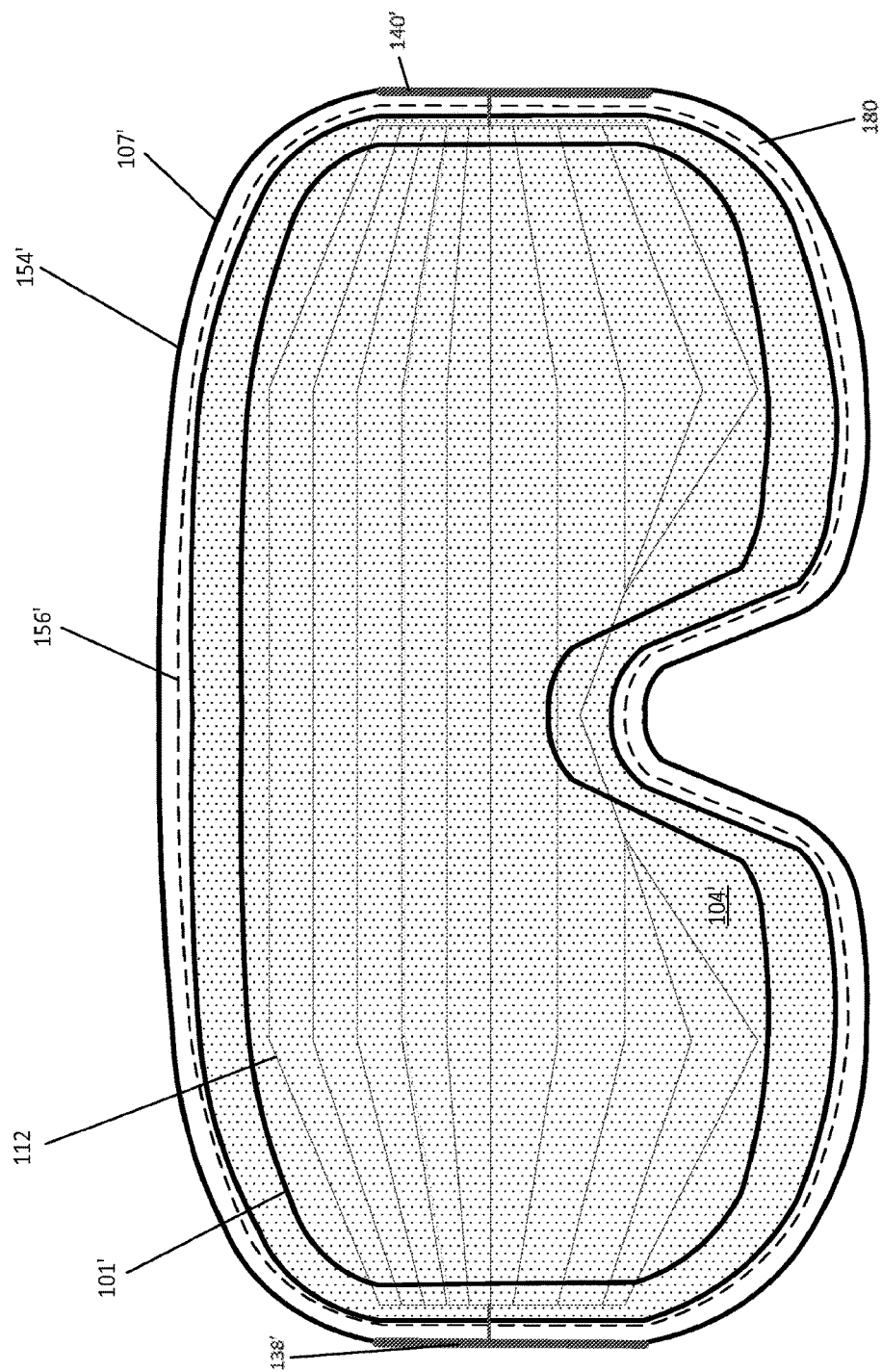
FIG. 3f is a front plan view of an alternate, differently-tinted, anti-fog lens/retaining/face contact member combination of a goggle in accordance with the second embodiment of the invention, the lens having resistive-wire anti-fog means thereon.
Figure 3G:
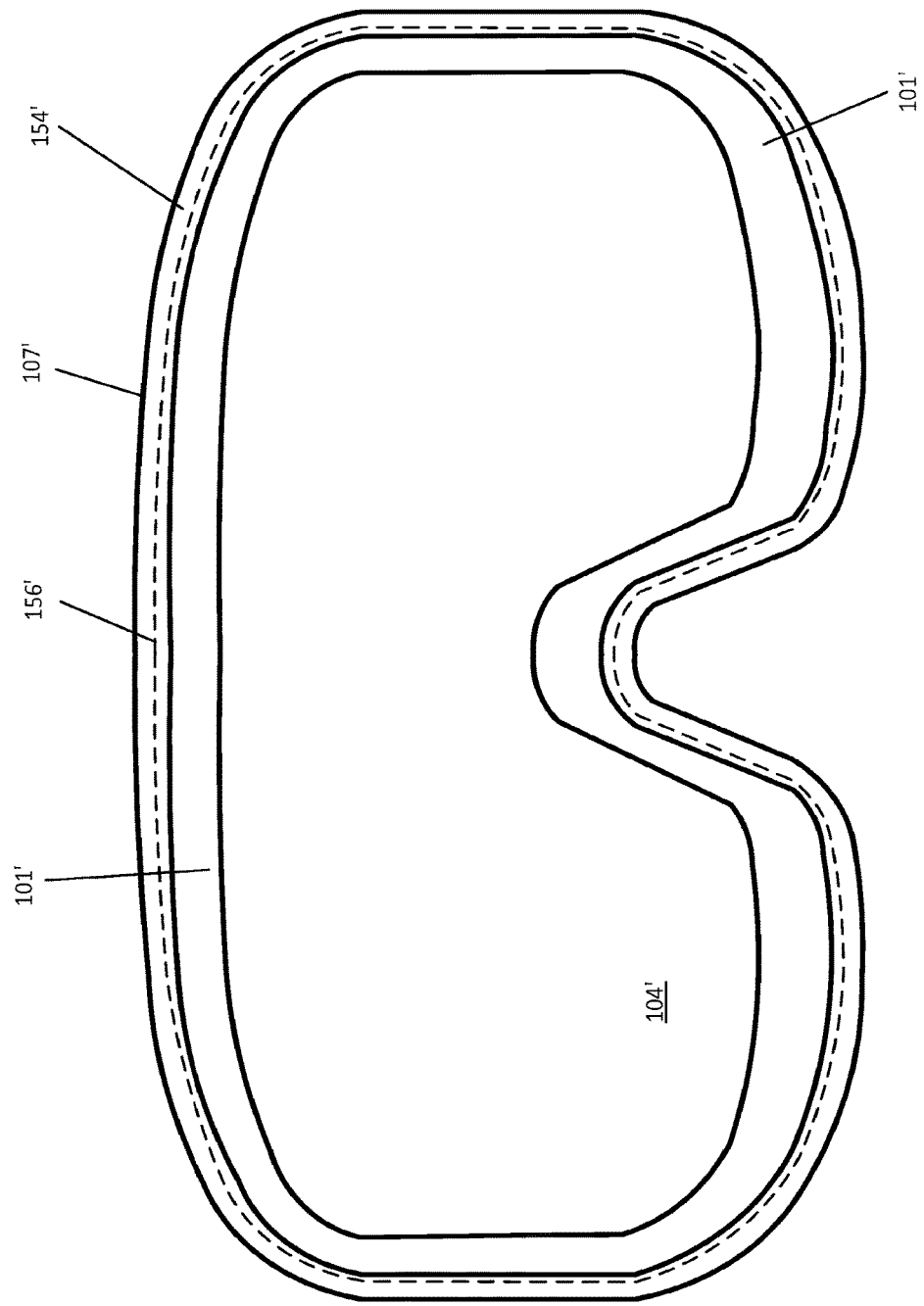
FIG. 3g is a front plan view of an alternate, non-tinted, lens/retaining/face contact member combination of a goggle in accordance with the second embodiment of the invention, the lens having no anti-fog means thereon.
Figure 4A:
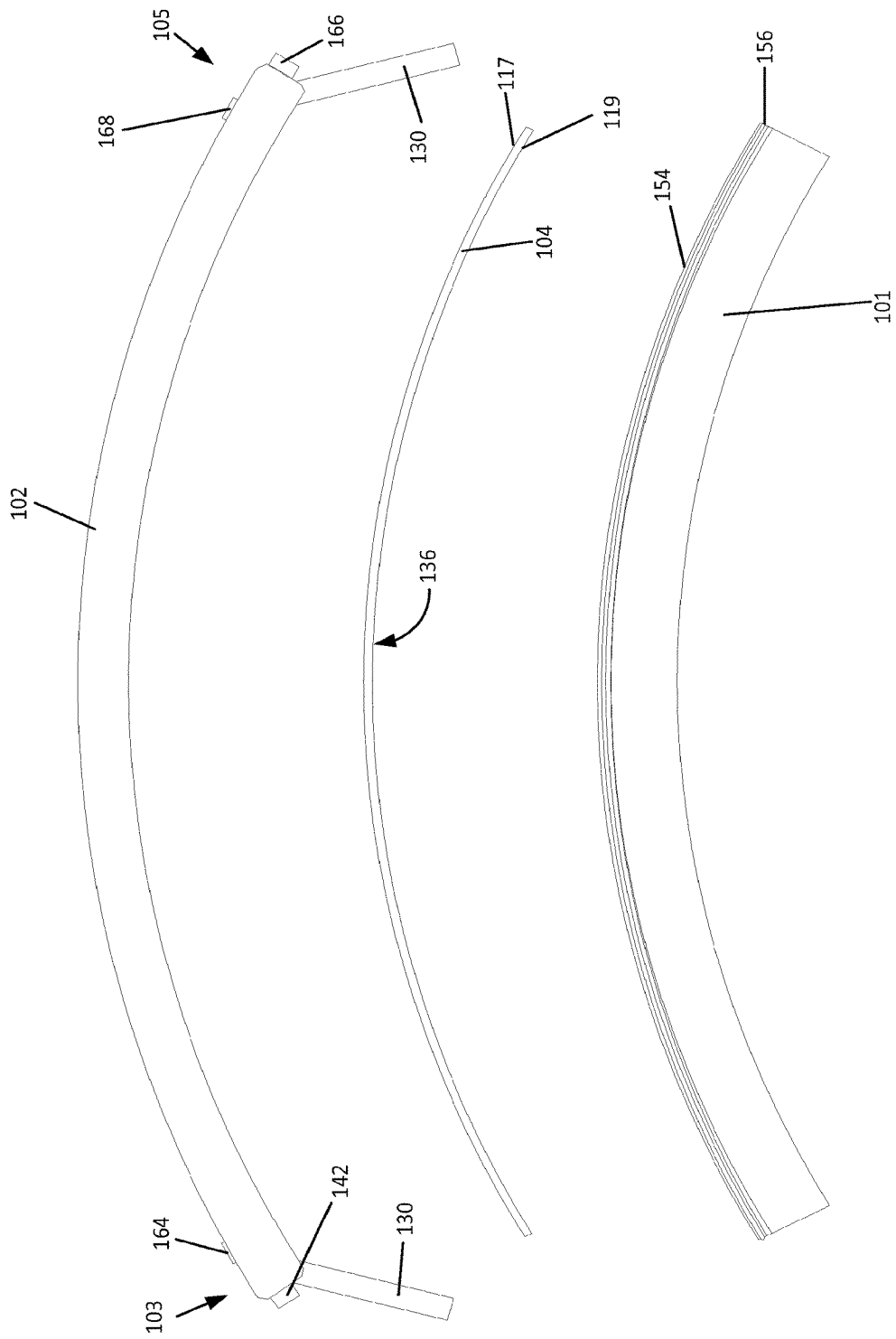
FIG. 4a is a top perspective exploded view of anterior goggle body, lens and posterior lens retaining member/face contact member parts of a goggle in accordance with the first embodiment of the present invention.
Figure 4B:
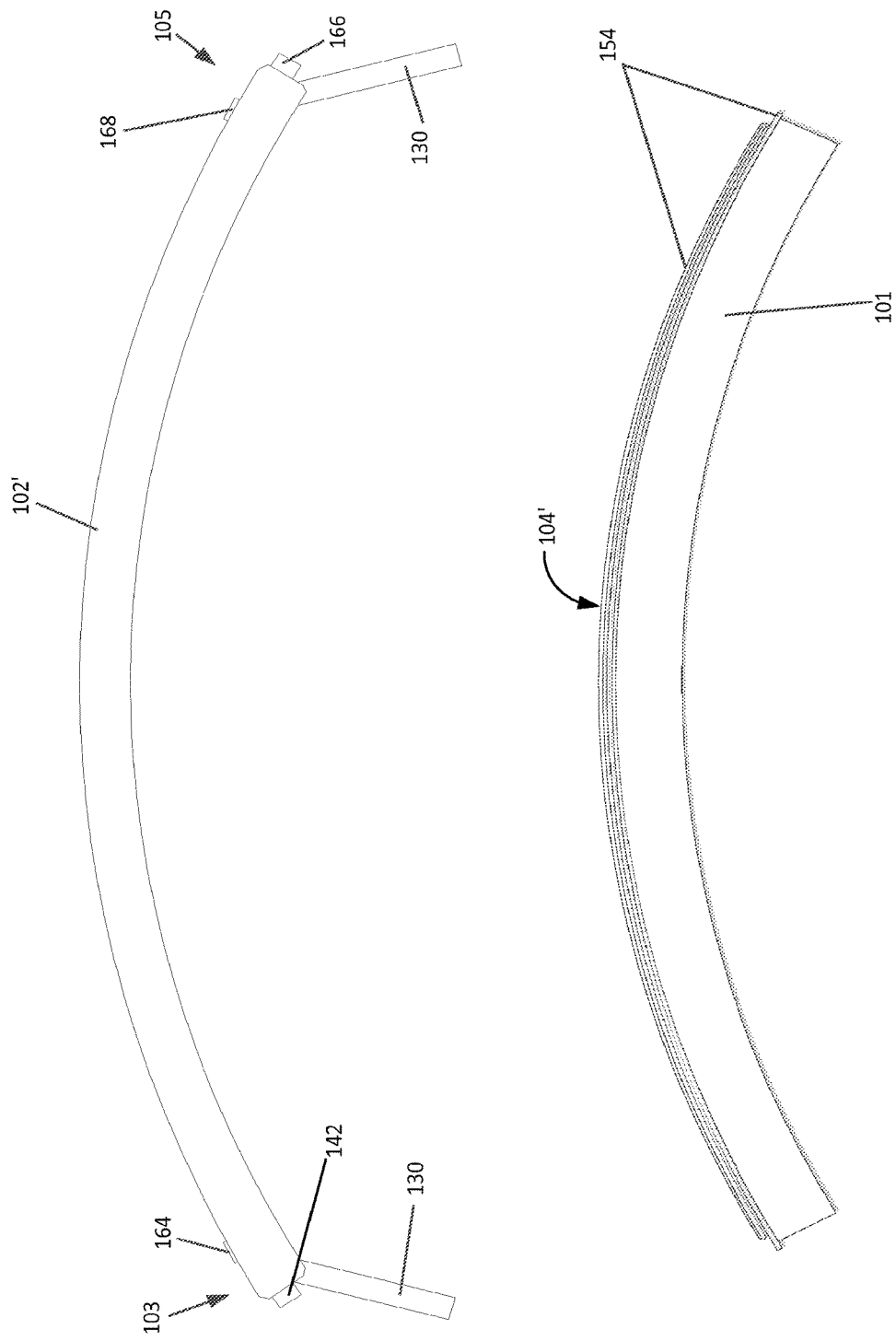
FIG. 4b is a top perspective exploded view of an anterior goggle body and lens/retaining/face contact member combination of a goggle in accordance with a second embodiment of the present invention.

As with the primary embodiment of the invention, this embodiment of the invention also provides for easy interchangeability of lenses 104' having various different characteristics with a goggle body 102'. Referring now to FIGS. 3e-g, there are shown front plan views of interchangeable combined lens 104'/face contact 101'/lens retaining member 154', described above, for use in accordance with the second embodiment of the invention, and showing that the tongue 156' preferably extends around the entire periphery of the lens retaining (or interconnection frame) member 154'.

FIG. 3e shows a lightly tinted lens portion 104' of a goggle 100' and having resistive-gel anti-fog means 112' thereon. The lens 104' has buss bar wires 111', 113' interconnecting the gel anti-fog means 112' with lens contacts 138', 140' carried on and adjacent a face plate 158' of the lens retaining member 154', respectively. The lens retaining member 154' has a peripheral edge 107' adapted for engagement with and retention within the receptacle 150' of the goggle body 102', where the lens contacts 138', 140' interconnect with the corresponding body contacts 139', 141'. Thus the lens 104'/face contact 101'/lens retaining member 154' is held into place in the receptacle 150' with the assistance of the tongue 156' and groove 152' interconnection means reinforced by a strap 110 that assists in holding the assembly of the goggle body 102' and the lens/face contact/lens retaining member together.

In FIG. 3e, a front plan view of the combined lens 104'/face contact 101'/lens retaining interface member 154' is shown comprising the tongue member 156' extending around the periphery of the interface member 154'. The tongue 156' is adapted for receipt in the groove 152' defined around the inner periphery of the goggle body 102'. The tongue member 156' is part of the interconnection means for retaining the lens 104' in the lens retaining receptacle 150' of the goggle body 102'. The interior periphery of the goggle body 102' is angled slightly inwardly, similar to a funnel configuration, so that the combined lens 104'/face contact 101'/lens retaining interface member 154' is guided into place to where it rests with tongue 156' retained in the groove 152'. Posterior of the interface member 154' and around the periphery of the interface member, there is attached a face contact member 101', preferably comprised of foam rubber, for making a comfortable seal against the user's face, and that is glued, or otherwise attached, to the posterior portion of the interface member.

FIG. 3e further shows a magnified detailed portion of the interface member 154' and tongue 156', the tongue being represented by three dashed lines in the detailed portion, one line for each side of the base of the tongue and one line for the ultimate tip of the tongue. Further, these three lines are represented as a single line extending around the periphery of the interface member 154' demonstrating that the tongue 156' preferably extends around the entire periphery of the interface member. It will be appreciated that, because of the somewhat irregular curvature of the lens 104'/interface 154'/face contact 101' member to adapt to the contours of a person's face, as is commonly understood in the goggle art, the lines representing the tongue 156 are for illustrative purposes, and the lines illustrating the tongue would at various points around the interface member be hidden by other lines for leading front edges of the interface member.

FIG. 3f shows an alternate shade tinted lens portion 104' of a goggle in accordance with the invention and having resistive-wire anti-fog means 112' thereon. The wires of the resistive-wire anti-fog means 112' of the lens 104' of FIG. 3f are interconnected by contacts 138', 140'. The peripheral edge 107' of the lens retaining member 154' of FIG. 3f is likewise adapted for engagement within the receptacle 150' of the goggle body 102'. A face plate part 180 of the lens retaining member 154' which is preferably integrally formed posterior and laterally adjacent the outer edge of the retaining member carries lens contacts 138', 140' for making electrical contact between the heating element 112' and the corresponding body contacts 139', 140' leading to the power circuit assembly, it being the case that the power circuit assembly is the same for this embodiment of the invention as for the previous embodiment of the invention. The lens 104' of FIG. 3f is likewise held into place in the receptacle 150' with the assistance of a strap 110 which reinforces the tongue 156' and groove 152' engagement and interconnection described previously.

FIG. 3g shows another alternate lens 104' without any tint and without any anti-fog means or related electrical contacts thereon. The peripheral edge 107' of the lens 104'/face contact 101'/lens retaining member 154' of this embodiment of the invention is likewise adapted for engagement and retention within the receptacle 150' of body 102' of the goggle 100' with the assistance of the tongue 156' and groove 152' engagement and interconnection means as shown in FIGS. 33 and 5d-f.

Referring now to FIG. 6c, showing a back view of the goggle body 102' (normal to the orientation of FIG. 5d), the groove 152' is shown as being defined around the entire inner periphery of the body. FIG. 6c also includes a magnified detailed portion of the groove 152' wherein the groove is represented by three dashed lines, whereas the groove as it extends around the inner periphery of the goggle body 102' is represented as a single dashed line for sake of clarity in illustration and because three dashed lines would be too close together to distinguish. The fourth, innermost, dashed line in FIG. 6c represents an inner edge 182 (corresponding to the reference point 182 as shown in FIG. 5d) of the body 102' partially defining the receptacle 150' in which the lens retaining member 154' resides. For added reference and understanding of the drawing, reference points 159' and 161' correspond to like reference points, or edges, on FIG. 5d. Other hidden lines are left off of drawing 6c for sake of clarity.

This aspect of the invention provides for easy interchangeability of differing tinted lenses 104' having anti-fog means 112' thereon, since, upon removal of the goggle from the user's head, the face contact 101'/retaining member 154' is able to be grabbed and removed from its interconnected engagement with the body 102'. This feature makes use of the goggle 100' more care-free, as whether the goggle is switched on, or off, the user is encouraged in choosing a goggle that suits the weather, terrain, and lighting conditions of the moment. Removal of the retaining member 154' may be facilitated by flexing the goggle body 102' and lens 104' combination in opposition to the natural curvature of the lens and goggle body to pop the seal between the tongue 156' of the retaining member and the groove 152' of the body 102'. Alternatively, a small pull tab or zip cord (not shown) may be added to the rear side of the retaining member 154' for facilitating and directing grabbing and removal of the lens 104'/face contact 101'/retaining member 154' combination.

Resistive-Wire Heating Element Version

In FIG. 3f, the heating element 112' is shown as a resistive-wire heating element preferably sandwiched with transparent glue between two lenses comprising a composite lens 104' as is known in the art. The resistive-wire heating element 112' branches from contacts 138', 140' with the contacts leading, upon installation of the lens 104' into the goggle body 102', to and from power control circuitry on the flexible circuit 148' as described previously.

Resistive-Gel Heating Element Version

In FIG. 3e, the heating element 112' is shown as a resistive-gel heating element with buss bar lead wires 111', 113' leading to and from the resistive-gel heating element and in contact with lens contacts 138', 140' that, upon installation of the combination lens 104'/face contact 101'/interface member 154' in the goggle body 102', connect with corresponding goggle body contacts 139', 141', as described above, to interconnect the resistive-gel heating element with the power circuit assembly described previously.

As is known in the art, the gel heating element 112 comprises a transparent conductive oxide heating element along with metal, such as silver, buss bar lead wires 111, 113, both of which are deposited on the lens 104 via DC magnetron sputtering process, ion-enhanced E-beam vaporization process, or pressure sensitive adhesive laminate onto a semi-rigid optical substrate, such as acrylic or polycarbonate, of the lens 104.

It will be appreciated that the basic configuration of the power electronics shown in FIGS. 5a-c, 6a and 8 apply whether the resistive-gel version of the lens 104 is utilized or the resistive-wire version of the lens 104 is utilized, though there would be some differences in the circuitry for one version over the other as will be apparent to those of ordinary skill in the art upon learning manufacturer specified power requirements for either type of heating element.

An object of the invention is to facilitate the use of anti-fog goggles with a number of easily interchangeable and different lenses having differing tint, anti-fog, vision correction and UV-filtering characteristics. Another object of the invention is to accomplish this in a goggle that is relatively inexpensive to manufacture and provide to the marketplace. The present invention addresses these objectives simply by making it easier for a user to interchange lenses in an anti-fog goggle in accordance with the invention, it being the case that upon installation of the alternative lens, contact is automatically made between the power and electronics of the goggle and the heating element 112 of the lens. Thus, via the interconnection means of the lens 104 and the goggle body 102, namely the tongue 156 and groove 152 defined on the lens and in the body, respectively, the lens 104 is secured to the body 102 simultaneously with the electrical interconnection between the anti-fog resistive means 112 and the battery-operated power source 114. Thus, this aspect of the invention facilitates a minimum of steps, at most one or two steps, for interconnection of a new lens 104 with the battery power source 114 such that users will be encouraged to use the same while engaging in the activity for which the goggle has been designed. In this way, the interconnection means is used to reinforce engagement of the lens 104 with the goggle body 102 and also provides for completion of the circuit for providing heat to the lens.

Regarding application of the present invention to vision correcting lenses 104, active heating of the lens with the heating element 112 overcomes dew point within the cavity formed between the lens and the user's face, thus preventing fogging of the lens, such that the greater volume and area requirements for passive anti-fogging of prior art lenses are not necessary. Thus the present invention allows for a consistent and smaller distance between the user's face and the lens 104 of the goggle than prior art passive anti-fog lenses, which in turn enables application of the present invention to corrective lens requirements that the corrective lens be close to the user's eyes and consistently spaced therefrom. Because the present invention is modular in allowing easy interchangeability of lenses, the invention is easily adapted for use with separately manufactured corrective, anti-fog lenses. Further, because the lens 104 of the present invention is in close proximity to the user's face, this enables greater field of peripheral vision for the user of the present invention.

While a preferred embodiment of the present invention has been shown and described, it will be apparent to those skilled in the art that many changes and modifications may be made without departing from the invention in its broader aspects. For example, it will be appreciated that one of ordinary skill in the art may mix and match the various components of the various embodiments of the invention without departing from the true spirit of the invention as claimed. Thus, by way of example, it will be appreciated that a cap-and-ridge engagement means may be interchanged with a tongue-and-groove engagement means in any embodiment without departing from the scope of the invention. Further, interchanging lens colors or disclosed anti-fog capability with alternate embodiment body or lens frame would likewise not depart from the spirit and scope of the invention. The appended claims are therefore intended to cover all such changes and modifications as fall within the true spirit and scope of the invention.

What is claimed is:

1. A modular, anti-fog goggle system comprising:
an interchangeable lens having an anti-fog heating element with a first electrical contact thereon and further comprising first and second ends, an anterior surface, a posterior surface, and a peripheral edge;
a semi-rigid anterior body comprising first and second ends and an inner peripheral receptacle, said lens being adapted for being releasably retained in said body a distance from a user's face and eyes so as to provide a shield for the eyes, the receptacle of said body adapted for receiving said lens within said body with a portion of the anterior surface of said lens that is adjacent the peripheral edge of said lens engaging the receptacle;
a battery adapted for electrical connection to the heating element on said lens;
a removable lens retaining member adapted for engaging a portion of the posterior surface of said lens that is adjacent the peripheral edge of said lens and adapted for releasably retaining said lens in the receptacle of said body;
tongue and groove mated retention means attached around said body and said lens retaining member, one of the tongue and groove of said tongue and groove mated retention means attached around a periphery of said body, and another of the tongue and groove of said tongue and groove mated retention means attached around a periphery of said lens retaining member for releasably interconnecting said lens with said body;
a second electrical contact on one of said body and said removable lens retaining member and connected with said battery, wherein upon installation of said removable lens retaining member into said body, the first electrical contact on said lens is releasably connected with the second electrical contact on one of said body and said lens retaining member adapted for allowing heating of said lens;
a flexible posterior interface attached to said removable lens retaining member adapted for engaging a user's face adjacent the user's eyes; and a strap having first and second ends, the first end of said strap interconnected with the first end of said body, and the second end of said strap interconnected with the second end of said body, adapted for holding the goggle on a user's head, said strap adapted for reinforcing retention of said lens in said body and contact of the electrical contacts on said lens with said battery.

2. The modular, anti-fog goggle system of claim 1, wherein the one of a tongue and groove of said tongue and groove mated retention means attached around the periphery of said body comprises a groove and the another of a tongue and groove of mated retention means attached around the periphery of said removable lens retaining member comprises a tongue, the groove and tongue portions attached around the periphery of said body and said lens retaining member being adapted for releasably interconnecting said body and said lens retaining member to retain said lens in said body and to retain said first contact on said lens in contact with said second electrical contact on one of said body and said removable lens retaining member and connected with said battery.

3. The modular, anti-fog goggle system of claim 1, wherein said battery is retained in said body.

4. The modular, anti-fog goggle system of claim 3, further comprising a battery strength indicator, comprising one of an array of LED's carried on said body, a plurality of light pipes adapted for directing light within the goggle, and an on-lens display.

5. The modular, anti-fog goggle system of claim 3, further comprising a heat adjustment switch on said body and circuitry in said body and connected with said battery.

6. The modular, anti-fog goggle system of claim 3, further comprising an on/off power switch on said body and connected with said battery.

* * * * *